United States Patent

Engelhardt et al.

[11] 4,119,710
[45] Oct. 10, 1978

[54] BRONCHOSPASMOLYTIC 1-(P-AMINO-PHENYL)-2-AMINO-ETHANOLS-(1) AND SALTS

[75] Inventors: Günther Engelhardt; Johannes Keck; Gerd Krüger, all of Biberach an der Riss; Klaus-Reinhold Noll, Warthausen-Oberhofen; Helmut Pieper, Biberach an der Riss, all of Fed. Rep. of Germany

[73] Assignee: Boehringer Ingelheim GmbH, Ingelheim am Rhein, Fed. Rep. of Germany

[21] Appl. No.: 754,981

[22] Filed: Dec. 28, 1976

Related U.S. Application Data

[63] Continuation-in-part of Ser. No. 426,949, Dec. 13, 1973, abandoned.

[30] Foreign Application Priority Data

Dec. 18, 1972 [DE] Fed. Rep. of Germany ....... 2261914
Sep. 8, 1973 [DE] Fed. Rep. of Germany ....... 2345442
Oct. 12, 1973 [DE] Fed. Rep. of Germany ....... 2351281

[51] Int. Cl.² ................. A61K 31/04; A61K 31/135; A61K 31/275; A61K 31/36
[52] U.S. Cl. ......................... 424/282; 260/340.5 R; 260/463; 260/465 E; 260/501.17; 260/562 P; 260/570.6; 424/304; 424/330; 560/27
[58] Field of Search ......... 260/465 E, 570.6, 340.5 R; 424/304, 330, 282

[56] References Cited

U.S. PATENT DOCUMENTS

3,536,712  10/1970  Keck et al. ............ 260/570.6 X
3,574,211  4/1971   Keck et al. ............ 260/570.6 X Primary Examiner—Dolph H. Torrence
Attorney, Agent, or Firm—Hammond & Littell

[57] ABSTRACT

Racemic and optically active compounds of the formula

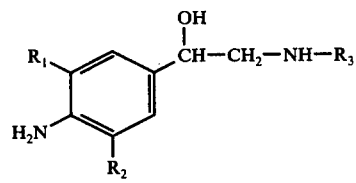

wherein
  $R_1$ is hydrogen, fluorine, chlorine, bromine, iodine or cyano,
  $R_2$ is fluorine, trifluoromethyl, nitro or cyano, and
  $R_3$ is alkyl of 3 to 5 carbon atoms, hydroxy(alkyl of 3 to 5 carbon atoms), cycloalkyl of 3 to 5 carbon atoms, 1-(3,4-methylenedioxy-phenyl)-2-propyl or 1-(p-hydroxy-phenyl)-2-propyl, and non-toxic, pharmacologically acceptable acid addition salts thereof; the compounds as well as their salts are useful as analgesics, uterospasmolytics, bronchospasmolytics and antispastics for the skeletal musculature, and especially as $\beta_2$-receptor mimetics and $\beta_1$-receptor blockers.

7 Claims, No Drawings

BRONCHOSPASMOLYTIC 1-(P-AMINO-PHENYL)-2-AMINO-ETHANOLS-(1) AND SALTS

This is a continuation-in-part of copending application Ser. No. 426,949 filed Dec. 13, 1973, now abandoned.

This invention relates to novel 1-(p-amino-phenyl)-2-amino-ethanols-(1) and acid addition salts thereof, as well as to various methods of preparing these compounds.

More particularly, the present invention relates to a novel class of racemic and optically active 1-(p-amino-phenyl)-2-amino-ethanols of the formula

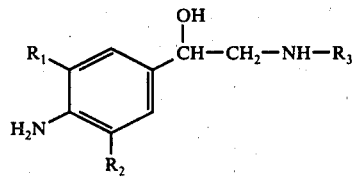

wherein
$R_1$ is hydrogen, fluorine, chlorine, bromine, iodine or cyano,
$R_2$ is fluorine, trifluoromethyl, nitro or cyano, and
$R_3$ is alkyl of 3 to 5 carbon atoms, hydroxy(alkyl of 3 to 5 carbon atoms), cycloalkyl of 3 to 5 carbon atoms, 1-(3,4-methylenedioxy-phenyl)-2-propyl or 1-(p-hydroxy-phenyl)-2-propyl,
and non-toxic, pharmacologically acceptable acid addition salts thereof.

A sub-genus thereunder is constituted by compounds of the formula I, where
$R_1$ and $R_3$ have the meanings defined above, and
$R_2$ is trifluoromethyl, nitro or cyano,
and non-toxic, pharmacologically acceptable acid addition salts thereof.

A further sub-genus thereunder is constituted by compounds of the formula I, where
$R_3$ has the meanings defined above,
$R_1$ is fluorine, chlorine, bromine, iodine or cyano, and
$R_2$ is trifluoromethyl, nitro or cyano,
and non-toxic, pharmacologically acceptable acid addition salts thereof.

The compounds embraced by formula I may be prepared by the following methods:

Method A

By reduction of an acetophenone of the formula

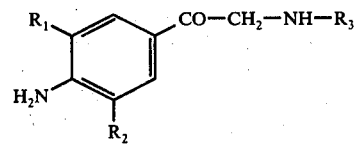

wherein $R_1$, $R_2$ and $R_3$ have the same meanings as in formula I.

The reduction is preferably carried out in a solvent, such as methanol, methanol/water, ethanol, isopropanol, ether, tetrahydrofuran or dioxane, either with a complex metal hydride, such as lithium aluminum hydride or sodium borohydride, or with aluminum isopropylate in the presence of a primary or secondary alcohol, or with catalytically activated hydrogen, at temperatures between −20° C. and the boiling point of the solvent which is used.

The reduction with a complex metal hydride is, however, preferably carried out with sodium borohydride at room temperature. If a reactive complex metal hydride, such as lithium aluminum hydride, is used and if the reduction is carried out at elevated temperatures, the cyano group mentioned in the definition of substituent $R_2$ may also be reduced at the same time.

Method B

For the preparation of a compound of the formula I, wherein $R_1$ is chlorine, bromine or iodine, by halogenation of a compound of the formula

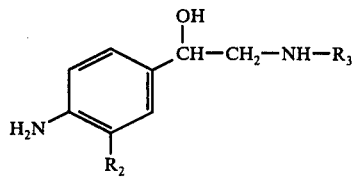

wherein $R_2$ and $R_3$ have the meanings defined above.

The reaction is carried out with a halogenating agent, such as chlorine, bromine, iodine, tribromophenolbromine or iodo benzene dichloride, preferably in a solvent, such as 50 to 100% acetic acid or in tetrahydrofuran in the presence of a tertiary organic base, and optionally in the presence of a heavy metal salt, such as mercury(II)oxide and at a temperature between 0° and 50° C. Per mol of a compound of the formula III, which may be used as base or also as its salt, such as its mono-, di- or trihydrochloride, 1 mol of the halogenating agent or a small excess thereover is employed. If a hydrogen halide salt is obtained during the reaction, the salt may be directly isolated or, if desired, it may be further purified by way of the base.

Method C

By removal of one or more protective groups from a compound of the formula

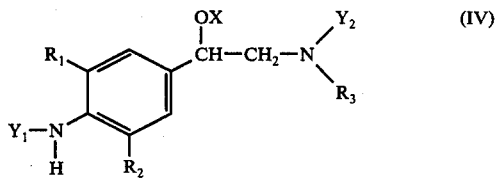

wherein $R_1$, $R_2$ and $R_3$ have the meanings defined in formula I, X is a protective group for a hydroxyl group or a hydrogen atom, $Y_1$ is a protective group for an amino group or a hydrogen atom, $Y_2$ is a protective group for an amino group or a hydrogen atom, where, however, at least one of X, $Y_1$ and/or $Y_2$ has to be one of the above-mentioned protective groups.

Especially preferred for $Y_1$ and/or $Y_2$ is the meaning of acyl, such as acetyl, benzoyl or p-toluenesulfonyl, or benzyl; and especially preferred for X is the meaning of acyl, such as acetyl, benzoyl or p-toluenesulfonyl, or trimethylsilyl, benzyl or tetrahydropyranyl-(2).

If $Y_1$ and/or $Y_2$, for example, represent acyl, the removal of this group is effected by hydrolysis, such as with ethanolic hydrochloric acid or with sodium hydroxide solution at temperatures up to the boiling point of the solvent which is used.

If X, Y₁ and/or Y₂, for example, represent benzyl in a compound of the formula IV, where R₂ is other than nitro, the removal of this benzyl group is effected hydrogenolytically, for example with hydrogen in the presence of a catalyst, such as palladized coal or palladium oxide hydrate on barium sulfate, platinum or Raney nickel, preferably in a solvent, such as methanol, methanol/hydrochloric acid or ethanol, at room temperature or at slightly elevated temperatures and at normal pressure or slightly elevated pressure.

If X, for example, represents acyl, trimethylsilyl or tetrahydropyranyl-(2), the removal of these radicals is carried out by hydrolysis, preferably in the presence of an acid, and at temperatures up to the boiling point of the solvent which is used.

Method D

For the preparation of a compound of the formula I, wherein R₁ is hydrogen, by dehalogenation of a compound of the formula

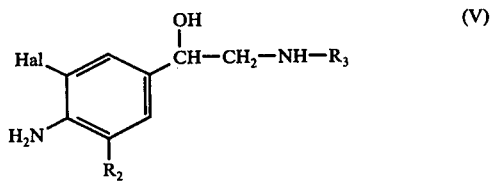

(V)

wherein R₂ and R₃ have the meanings defined in formula I, and Hal is chlorine, bromine or iodine.

The dehalogenation is preferably carried out in a solvent, advantageously either with triphenylphosphine in benzene or toluene, or with hydrogen in methanol, ethanol, ethyl acetate or tetrahydrofuran, and in the presence of a hydrogenation catalyst. Depending upon which method is used, the reaction is carried out at room temperature or at elevated temperatures, for example at temperatures between 100° and 150° C., and at a normal pressure or at a moderately elevated pressure; if, for example, Raney-nickel or palladized charcoal is used as the catalyst, the dehalogenation is performed at room temperature and at normal pressure.

If, in a compound of the formula V, R₂ represents nitro, the dehalogenation is preferably carried out with triphenylphosphine.

A racemate of the d,l-form of a compound of the formula I may be divided into its optically active components, preferably by fractional crystallization of a mixture of their diastereomeric salts with an optically active acid, such as with D(−)-tartaric acid, L(+)-tartaric acid, dibenzoyl-D-tartaric acid, dibenzoyl-L-tartaric acid, (+)-camphor-10-sulfonic acid, L(−)-malic acid, L(+)-mandelic acid, d-α-bromocamphor-π-sulfonic acid or l-quinic acid. The resolution of the racemate into its optically active components may, however, also be effected by column-chromatography with an optically active carrier, such as acetyl cellulose.

A compound of the formula I may be converted, if desired, into an acid addition salt thereof with 1, 2 or 3 equivalents of an inorganic or organic acid. Examples of non-toxic, pharmacologically acceptable acid addition salts are those formed with hydrochloric acid, hydrobromic acid, sulfuric acid, phosphoric acid, lactic acid, citric acid, tartaric acid, maleic acid, fumaric acid, 8-chlorotheophylline or the like.

The starting compounds of the formulas II to V may be obtained by methods described in the literature.

Thus, a starting compound of the formula II may, for example, be obtained by reaction of a corresponding 2-haloacetophenone with a corresponding amine.

The compounds of the formulas III, IV and V are obtained by reaction of a corresponding 2-haloacetophenone with the corresponding amine and subsequent reduction of the resulting ketones, for example with sodium borohydride; a starting compound of the formula IV may also be obtained by halogenation of the corresponding unhalogenated compound, or by catalytic reduction of a corresponding 4-nitro-phenyl compound.

The starting compounds of the formulas II to V for methods A to D need not be purified in all cases; they may also be used as crude products.

The following examples illustrate the present invention and will enable others skilled in the art to understand it more completely. It should be understood, however, that the invention is not limited solely to the particular examples given below.

EXAMPLE 1

1-(4'-Amino-3'-chloro-5'-trifluoromethyl-phenyl)-2-tert.butylamino-ethanol hydrochloride by method A 80 gm of 4'-amino-2-tert.butylamino-3'-chloro-5'-trifluoromethyl-acetophenone hydrochloride (decomposition between 223° and 231° C.) were dissolved in 500 ml of methanol, and the solution was cooled to −15° C. 9.5 gm of sodium borohydride were added in small portions over a period of one hour, while stirring and maintaining the temperature between −5° to −15° C. After one hour more of stirring at −15° C., the mixture was acidified with 2N hydrochloric acid, and the methanol was removed in vacuo. The remaining aqueous solution was made alkaline with 2N ammonia and was then extracted with ethyl acetate. The organic layer was washed with water, dried, and 50 ml of 4.5N isopropanolic hydrochloric acid were added. The precipitated hydrochloride of the above-mentioned substance was suction-filtered off and washed with ethyl acetate and ether. M.p. 205°–207° C. (decomp.). By concentration of the filtrate a further amount of the product was obtained.

EXAMPLE 2

1-(4'-Amino-3'-bromo-5'-cyano-phenyl)-2-dimethylamino-ethanol hydrochloride by method A 15.2 gm of 4'-amino-3'-bromo-5'-cyano-2-dimethylamino-acetophenone were dissolved in 300 ml of methanol, and a solution of 10 gm of sodium borohydride in 100 ml of water was added dropwise at room temperature while stirring. The solution was allowed to stand overnight, the excess sodium borohydride was destroyed by acidification with hydrochloric acid, the methanol was evaporated in vacuo, and the residue was dissolved in water. The aqueous solution was made alkaline with ammonia, extracted three times with about 150 ml of chloroform each, the combined chloroform solutions were washed twice with a small quantity of water, dried over sodium sulfate, and evaporated to dryness.

The residue was dissolved in ethanol, and the solution was weakly acidified with ethanolic hydrochloric acid, whereupon 1-(4'-amino-3'-bromo-5'-cyano-phenyl)-2-dimethylamino-ethanol hydrochloride was obtained. The reaction product was recrystallized from ethanol. M.p. 187°–190° C.

EXAMPLE 3

1-(4'-Amino-3'-chloro-5'-trifluoromethyl-phenyl)-2-tert.pentylamino-ethanol hydrochloride by method B 0.37 gm of 1-(4'-amino-3'-trifluoromethyl-phenyl)-2-tert.pentylamino-ethanol hydrobromide and 0.2 ml of pyridine were dissolved in 30 ml of tetrahydrofuran, and the solution was cooled to 0° C. 0.3 gm of iodobenzene dichloride was added, the mixture was held for 2 hours at 0° C., and 0.1 gm of iodobenzene dichloride was again added. After standing for 20 hours at about 4° C., the solution was evaporated, distributed between ethyl acetate and water, the aqueous phase was made alkaline with 2N ammonia, and the solution was again extracted with ethyl acetate. The organic phase was washed with water, dried and a few drops of isopropanolic 4N hydrochloric acid were added. The precipitated hydrochloride of the above-mentioned compound was suction-filtered off and washed with ether. M.p. 176°–178° C. (decomp.).

EXAMPLE 4

1-(4'-Amino-3'-trifluoromethyl-phenyl)-2-tert.butylamino-ethanol by method C 5.05 gm of 1-(4'-acetylamino-3'-trifluoromethyl-phenyl)-2-tert.butylamino-ethanol hydrochloride were refluxed for 3 hours in a mixture of 50 ml of ethanol and 50 ml of 4N sodium hydroxide. The ethanol was removed in vacuo, and the precipitated crystals were suction-filtered off, yielding the above-named free base. M.p. 145°–147° C. (from ethanol/water).

For conversion into the monohydrochloride, the base was dissolved in the calculated quantity of 1N hydrochloric acid; the mixture was evaporated to dryness in vacuo, and the solid residue was recrystallized from isopropanol/ether. M.p. of the hydrochloride 172°–174° C. (decomp.).

EXAMPLE 5

1-(4'-Amino-3'-trifluoromethyl-phenyl)-2-tert.butylamino ethanol by method C 0.45 gm of 1-(4'-amino-3'-trifluoromethyl-phenyl)-2-(N-benzyl-N-tert.butylamino)-ethanol were dissolved in 10 ml of methanol and 1.4 ml of 1N hydrochloric acid, and the solution was hydrogenated in a hydrogenation vessel in the presence of 50 mgm of palladium/coal-catalyst (10%) until 1 mol of hydrogen had been absorbed. The catalyst was removed by filtration, the filtrate was evaporated in vacuo, and the residue was distributed between ethyl acetate and 2N ammonia. The organic layer was washed with water, dried and again evaporated in vacuo. The residue was crystallized from ethanol/water. M.p. 145°–147° C.

EXAMPLE 6

1-(4'-Amino-3'-chloro-5'-trifluoromethyl-phenyl)-2-tert.butylamino-ethanol hydrochloride by method C 0.76 gm of 1-(4'-amino-3'-chloro-5'-trifluoromethyl-phenyl)-2-(N-benzyl-N-tert.butylamino)-ethanol were dissolved in 20 ml of methanol and 1.95 ml of 1N hydrochloric acid, and the solution was hydrogenated in a hydrogenation vessel in the presence of 80 mgm of palladium/coal-catalyst (10%) until 1 mol of hydrogen had been absorbed. Afterwards, the catalyst was removed by filtration, and the filtrate was evaporated to dryness in vacuo. The oily residue was purified by column chromatography (silicagel; chloroform:methanol:-concentrated ammonia = 80:20:1 as eluant). The fractions containing the desired substance were combined, and the solvent was removed in vacuo. The remaining crystalline base of the desired compound was converted into its hydrochloride with the calculated quantity of 1.07 N hydrochloric acid in isopropanol, and recrystallized from ethyl acetate/ether. M.p. 205°–207° C. (decomp.).

EXAMPLE 7

1-(4'-Amino-3'-trifluoromethyl-phenyl)-2-cyclopropylamino-ethanol dihydrochloride by method D 4.1 gm of 1-(4'-amino-3'-bromo-5'-trifluoromethyl-phenyl)-2-cyclopropylamino-ethanol were dissolved in 200 ml of methanol, and 2 gm of palladium oxide/barium sulfate catalyst (5%) were added. The mixture was hydrogenated in a hydrogenation vessel until 1 mol of hydrogen had been absorbed, the catalyst was filtered off, and the filtrate was evaporated to dryness in vacuo. The residue was dissolved in water, the solution was made alkaline with 2N ammonia, and the aqueous layer was extracted with ethyl acetate. The organic extracts were washed with water, dried and evaporated again. The solid residue was dissolved in isopropanol, and 2 equivalents of isopropanolic 4N hydrochloric acid were added to the solution. The crystallized dihydrochloride of the above-named compound was suction-filtered off and washed with isopropanol and ether. M.p. 141.5°–142° C. (decomp.).

EXAMPLE 8

1-(4'-Amino-3'-trifluoromethyl-phenyl)-2-tert.pentylamino-ethanol hydrobromide by method D 5 gm of 1-(4'-amino-3'-bromo-5'-trifluoromethyl-phenyl)-2-tert.pentylamino-ethanol hydrochloride were distributed between ethyl acetate and 2N ammonia. The organic layer was dried and evaporated in vacuo, the residual base was dissolved in 100 ml of methanol in a hydrogenation vessel. 2.5 gm of palladium oxide/barium sulfate catalyst (5%) were added, and the mixture was hydrogenated until 1 mol of hydrogen had been absorbed. After the catalyst had been removed by filtration, the filtrate was evaporated in vacuo, and the solid residue was recrystallized from isopropanol. The obtained hydrobromide melted at 174°–175° C. (decomp.).

EXAMPLE 9

1-(4'-Amino-3'-fluoro-phenyl)-2-tert.butylamino-ethanol, m.p. of the hydrochloride: 196°–197° C. (decomp.), was prepared from 4'-amino-2-tert.butylamino-3'-fluoro-acetophenone hydrochloride and sodium borohydride analogous to Example 1.

EXAMPLE 10

1-(4'-Amino-3'-bromo-5'-fluoro-phenyl)-2-tert.butylamino-ethanol, m.p. of the hydrochloride: 207°–208° C. (decomp.), was prepared from 4'-amino-3'-bromo-2-tert.butylamino-5'-fluoroacetophenone hydrochloride and sodium borohydride analogous to Example 1.

EXAMPLE 11

1-(4'-Amino-3'-chloro-5'-trifluoromethyl-phenyl)-2-cyclobutylamino-ethanol, m.p. of the hydrochloride: 177°–178° C., was prepared from 4'-amino-3'-chloro-2-cyclobutylamino-5'-trifluoromethyl-acetophenone hydrochloride and sodium borohydride analogous to Example 1.

EXAMPLE 12

1-(4'-Amino-3'-fluoro-phenyl)-2-cyclopropylamino-ethanol, m.p. of the hydrochloride: 157°–158° C. (decomp.), was prepared from 1-(4'-acetylamino-3'-fluoro-phenyl)-2-cyclopropylamino-ethanol analogous to Example 4.

EXAMPLE 13

1-(4'-Amino-3'-fluoro-phenyl)-2-tert.butylamino-ethanol, m.p. of the hydrochloride: 196°–197° C. (decomp.), was prepared from 1-(4'-amino-3'-fluoro-phenyl)-2-(N-benzyl-N-tert.butyl)-amino-ethanol hydrochloride analogous to Example 6.

EXAMPLE 14

1-(4'-Amino-3'-chloro-5'-fluoro-phenyl)-2-isopropylamino-ethanol, m.p. of the hydrochloride: 152°–154° C. (decomp.), was prepared from 4'-amino-3'-chloro-5'-fluoro-2-isopropylamino-acetophenone hydrochloride and sodium borohydride analogous to Example 1.

EXAMPLE 15

1-(4'-Amino-3'-chloro-5'-fluoro-phenyl)-2-cyclopropylamino-ethanol, m.p. of the hydrochloride: 175°–177° C. (decomp.), was prepared from 4'-amino-3'-chloro-2-cyclopropylamino-5'-fluoro-acetophenone hydrochloride and sodium borohydride analogous to Example 1.

EXAMPLE 16

1-(4'-Amino-3'-chloro-5'-fluoro-phenyl)-2-tert.butylamino-ethanol, m.p. of the hydrochloride: 206°–208° C. (decomp.), was prepared from 4'-amino-2-tert.butylamino-3'-chloro-5'-fluoro-acetophenone hydrochloride and sodium borohydride analogous to Example 1.

EXAMPLE 17

1-(4'-Amino-3'-chloro-5'-fluoro-phenyl)-2-tert.pentylamino-ethanol, m.p. of the hydrochloride: 187°–188° C. (decomp.), was prepared from 4'-amino-3'-chloro-5'-fluoro-2-tert.pentylamino-acetophenone hydrochloride and sodium borohydride analogous to Example 1.

EXAMPLE 18

1-(4'-Amino-3'-chloro-5'-fluoro-phenyl)-2-[1''-(3,4-methylenedioxy-phenyl)-2''-propylamino]-ethanol, m.p. of the hydrochloride: 119°–121° C. (decomp.), was prepared from 4'-amino-3'-chloro-5'-fluoro-2-[1''-(3,4-methylenedioxy-phenyl)-2''-propylamino]-acetophenone hydrochloride and sodium borohydride analogous to Example 1.

EXAMPLE 19

1-(4'-Amino-3'-bromo-5'-fluoro-phenyl)-2-isopropylamino-ethanol, m.p. of the hydrochloride: 171°–173° C. (decomp.), was prepared from 4'-amino-3'-bromo-5'-fluoro-2-isopropylamino-acetophenone hydrochloride and sodium borohydride analogous to Example 1.

EXAMPLE 20

1-(4'-Amino-3'-bromo-5'-fluoro-phenyl)-2-cyclopropylamino-ethanol, m.p. of the hydrochloride: 185°–187° C. (decomp.), was prepared from 4'-amino-3'-bromo-2-cyclopropylamino-5'-fluoro-acetophenone and sodium borohydride analogous to Example 1.

EXAMPLE 21

1-(4'-Amino-3'-bromo-5'-fluoro-phenyl)-2-(hydroxy-tert.butylamino)-ethanol, m.p. 122°–125° C., was prepared from 4'-amino-3'-bromo-5'-fluoro-2-(hydroxy-tert.butylamino)-acetophenone hydrochloride and sodium borohydride analogous to Example 1.

EXAMPLE 22

1-(4'-Amino-3'-bromo-5'-fluoro-phenyl)-2-tert.pentylamino-ethanol, m.p. of the hydrochloride: 185°–187° C. (decomp.), was prepared from 4'-amino-3'-bromo-5'-fluoro-2-tert.pentylamino-acetophenone hydrochloride and sodium borohydride analogous to Example 1.

EXAMPLE 23

1-(4'-Amino-3'-bromo-5'-fluoro-phenyl)-2-[1''-(3,4-methylenedioxy-phenyl)-2''-propylamino]-ethanol, m.p. 126°–128° C., was prepared from 4'-amino-3'-bromo-5'-fluoro-2-[1''-(3,4-methylenedioxy-phenyl)-2''-propylamino]-acetophenone and sodium borohydride analogous to Example 1.

EXAMPLE 24

1-(4'-Amino-3'-chloro-5'-trifluoromethyl-phenyl)-2-isopropylamino-ethanol, m.p. 104°–106° C., m.p. of the hydrochloride: 185°–187° C., was prepared from 4'-amino-3'-chloro-2-isopropylamino-5'-trifluoromethyl-acetophenone hydrochloride and sodium borohydride analogous to Example 1.

EXAMPLE 25

1-(4'-Amino-3'-chloro-5'-trifluoromethyl-phenyl)-2-cyclopropylamino-ethanol, m.p. 138°–139° C., was prepared from 4'-amino-3'-chloro-2-cyclopropylamino-5'-trifluoromethyl-acetophenone and sodium borohydride analogous to Example 1.

EXAMPLE 26

1-(4'-Amino-3'-chloro-5'-trifluoromethyl-phenyl)-2-hydroxy-tert.butylamino)-ethanol, m.p. of the hydrochloride: 219°–220° C., was prepared from 4'-amino-3'-chloro-2-(hydroxy-tert.butylamino)-5'-trifluoromethyl-acetophenone hydrochloride and sodium borohydride analogous to Example 1.

EXAMPLE 27

1-(4'-Amino-3'-chloro-5'-trifluoromethyl-phenyl)-2-tert.pentylamino-ethanol, m.p. of the hydrochloride: 176°–178° C. (decomp.), was prepared from 4'-amino-3'-chloro-2-tert.pentylamino-5'-trifluoromethyl-acetophenone hydrochloride and sodium borohydride analogous to Example 1.

EXAMPLE 28

1-(4'-Amino-3'-chloro-5'-trifluoromethyl-phenyl)-2-[2''-methyl-4''-hydroxy-butyl-(2'')-amino]-ethanol, m.p. of the hydrochloride: 148°–150° C. (decomp.), was prepared from 4'-amino-3'-chloro-2-[2''-methyl-4''-hydroxy-butyl-(2'')-amino]-5'-trifluoro-methyl-acetophenone and sodium borohydride analogous to Example 1.

EXAMPLE 29

1-(4'-Amino-3'-chloro-5'-trifluoromethyl-phenyl)-2-[1''-(3,4-methylenedioxy-phenyl)-2''-propylamino]-ethanol, m.p. of the hydrochloride: 206°–207° C. (decomp.), was prepared from 4'-amino-3'-chloro-2-[1''-(3,4-methylenedioxy-phenyl)-2''-propylamino]-5'-trifluoromethyl-acetophenone hydrochloride and sodium borohydride analogous to Example 1.

EXAMPLE 30

1-(4'-Amino-3'-bromo-5'-trifluoromethyl-phenyl)-2-isopropylamino-ethanol, m.p. 102°–103° C., m.p. of the hydrochloride: 177°–179° C. (decomp.), was prepared from 4'-amino-3'-bromo-2-isopropylamino-5'-trifluoromethyl-acetophenone hydrochloride and sodium borohydride analogous to Example 1.

EXAMPLE 31

1-(4'-Amino-3'-bromo-5'-trifluoromethyl-phenyl)-2-cyclopropylamino-ethanol, m.p. 141.5°–142.5° C., m.p. of the hydrochloride: 195°–195.5° C. (decomp.), was prepared from 4'-amino-3'-bromo-2-cyclopropylamino-5'-trifluoromethyl-acetophenone hydrochloride and sodium borohydride analogous to Example 1.

EXAMPLE 32

1-(4'-Amino-3'-bromo-5'-trifluoromethyl-phenyl)-2-tert.butylamino-ethanol, m.p. 85°–87° C., m.p. of the hydrochloride: 205°–206° C. (decomp.), was prepared from 4'-amino-3'-bromo-2-tert. butylamino-5'-trifluoromethyl-acetophenone hydrochloride and sodium borohydride analogous to Example 1.

EXAMPLE 33

1-(4'-Amino-3'-bromo-5'-trifluoromethyl-phenyl)-2-cyclobutylamino-ethanol, m.p. of the hydrochloride: 189°–191° C. (decomp.), was prepared from 4'-amino-3'-bromo-2-cyclobutylamino-5'-trifluoromethyl-acetophenone hydrochloride and sodium borohydride analogous to Example 1.

EXAMPLE 34

1-(4'-Amino-3'-bromo-5'-trifluoromethyl-phenyl)-2-tert.pentyl-amino-ethanol, m.p. of the hydrochloride: 166.5°–168° C. (decomp.), was prepared from 4'-amino-3'-bromo-2-tert.pentylamino-5'-trifluoromethyl-acetophenone hydrochloride and sodium borohydride analogous to Example 1.

EXAMPLE 35

1-(4'-Amino-3'-chloro-5'-cyano-phenyl)-2-isopropylamino-ethanol, m.p. of the hydrochloride: 185°–188° C., was prepared from 4'-amino-3'-chloro-5'-cyano-2-isopropylamino-acetophenone and sodium borohydride analogous to Example 2.

EXAMPLE 36

1-(4'-Amino-3'-chloro-5'-cyano-phenyl)-2-tert.butylamino-ethanol, m.p. 125°–133° C., was prepared from 4'-amino-3'-chloro-5'-cyano-2-tert.butylamino-acetophenone and sodium borohydride analogous to Example 2.

EXAMPLE 37

1-(4'-Amino-3'-bromo-5'-cyano-phenyl)-2-isopropylamino-ethanol, m.p. of the hydrochloride: 186°–189° C., was prepared from 4'-amino-3'-bromo-5'-cyano-2-isopropylamino-acetophenone and sodium borohydride analogous to Example 2.

EXAMPLE 38

1-(4'-Amino-3'-bromo-5'-cyano-phenyl)-2-tert.butylamino-ethanol, m.p. of the hydrochloride: 213°–214° C., was prepared from 4'-amino-3'-bromo-2-tert.butylamino-5'-cyano-acetophenone and sodium borohydride analogous to Example 2.

EXAMPLE 39

1-(4'-Amino-3'-fluoro-phenyl)-2-isopropylamino-ethanol, m.p. of the hydrochloride: 156°–158° C. (decomp.), was prepared from 1-(4'-acetylamino-3'-fluoro-phenyl)-2-isopropylamino-ethanol analogous to Example 4.

EXAMPLE 40

1-(4'-Amino-3'-fluoro-phenyl)-2-tert.pentylamino-ethanol, m.p. of the hydrochloride: 153°–155° C. (decomp.), was prepared from 1-(4'-acetylamino-3'-fluoro-phenyl)-2-tert.pentylaminoethanol analogous to Example 4.

EXAMPLE 41

1-(4'-Amino-3'-trifluoromethyl-phenyl)-2-isopropylamino-ethanol, m.p. 136°–137.5° C., was prepared from 1-(4'-amino-3'-bromo-5'-trifluoromethyl-phenyl)-2-isopropylamino-ethanol analogous to Example 7.

EXAMPLE 42

1-(4'-Amino-3'-cyano-phenyl)-2-isopropylamino-ethanol, m.p. 159°–161° C., was prepared from 1-(4'-amino-3'-bromo-5'-cyanophenyl)-2-isopropylamino-ethanol analogous to Example 7.

EXAMPLE 43

1-(4'-Amino-3'-cyano-phenyl)-2-tert.butylamino-ethanol, m.p. 181°–185° C., was prepared from 1-(4'-amino-3'-bromo-5'-cyanophenyl)-2-tert.butylamino-ethanol analogous to Example 7.

EXAMPLE 44

1-(4'-Amino-3'-chloro-5'-trifluoromethyl-phenyl)-2-tert.butyl-amino-ethanol, m.p. of the hydrochloride: 205°–207° C. (decomp.), was prepared from 2-tert.butylamino-1-[3'-chloro-4'-(p-chloro-benzoylamino)-5'-trifluoromethyl-phenyl]-ethanol analogous to Example 4.

EXAMPLE 45

1-(4'-Amino-3'-fluoro-phenyl)-2-tert.butylamino-ethanol, m.p. of the hydrochloride: 196°–197° C. (decomp.), was prepared from 1-(4'-benzoylamino-3'-fluoro-phenyl)-2-tert.butylamino-ethanol analogous to Example 4.

EXAMPLE 46

1-(4'-Amino-3'-chloro-5'-fluoro-phenyl)-2-tert.butylamino-ethanol, m.p. of the hydrochloride: 206°–208° C. (decomp.), was prepared from 2-tert.butylamino-1-(3'-chloro-5'-fluoro-4'-propionylamino-phenyl)-ethanol analogous to Example 4.

EXAMPLE 47

1-(4'-Amino-3'-bromo-5'-trifluoromethyl-phenyl)-2-cyclopentyl-amino-ethanol, m.p. 100°–102.5° C. (decomp.), was prepared from 4'-amino-3'-bromo-2-cyclopentylamino-5'-trifluoromethylacetophenone hydrochloride and sodium borohydride analogous to Example 1.

EXAMPLE 48

1-(4'-Amino-3'-bromo-5'-cyano-phenyl)-2-cyclopropylamino-ethanol by method A 3 gm of sodium borohydride were added at room temperature to a solution of 7.5 gm of 4'-amino-3'-bromo-5'-cyano-2-cyclopropylamino-acetophenone in 200 ml of tetrahydro-furan and 100 ml of water, and the mixture was stirred for one hour. Thereafter, the excess sodium borohydride was destroyed by addition of acetone. The insoluble part of the mixture was filtered off, and the solvents were distilled out of the filtrate in vacuo. The residue was dissolved in hot isopropanol, and the hydrochloride of 1-(4'-amino-3'-bromo-5'-cyano-phenyl)-2-cyclopropylanino-ethanol was precipitated by addition of isopropanolic hydrochloric acid, and recrystallized from isopropanol. M.p. 190°–193° C. (decomp.).

EXAMPLE 49

1-(4'-Amino-3'-bromo-5'-fluoro-phenyl)-2-cyclobutylamino-ethanol by method A (a) 20 gm of 4'-amino-3'-bromo-5'-fluoro-acetophenone were dissolved in 300 ml of chloroform, the solution was heated to the boiling point, and then a solution of 4.3 ml of bromine in 20 ml of chloroform was slowly added dropwise while stirring. Afterwards, the mixture was stirred for five minutes more at the boiling point and was then cooled to room temperature. To the resulting solution of raw 4'-amino-3',2-dibromo-5'-fluoro-acetophenone, a mixture of 15 gm of cyclobutylamine and 14 ml of triethylamine was added dropwise while stirring and cooling on ice. Afterwards, the mixture was refluxed for two hours, allowed to cool and washed with water. The organic layer was evaporated to dryness in vacuo. The residue consisted of raw 4'-amino-3'-bromo-2-cyclobutylamino-5'-fluoro-acetophenone.

(b) The raw ketone obtained in step a) was dissolved in 30 ml of tetrahydrofuran, 5 ml of water were added to the solution, and then 4.5 gm of sodium borohydride were added in small portions while stirring and cooling on ice. The resulting solution was stirred for 3 hours, while cooling, and was then allowed to stand overnight at room temperature. Subsequently, the excess sodium borohydride was destroyed with acetone, and the solution was evaporated to dryness in vacuo. The residue was distributed between water and chloroform, the organic layer was extracted three times with 100 ml of 2N hydrochloric acid each, and the combined hydrochloric acid extracts were made alkaline with sodium hydroxide and extracted with chloroform. The chloroform solution was washed with water, dried over sodium sulfate and evaporated to dryness in vacuo. The residue of raw 1-(4'-amino-3'-bromo-5'-fluorophenyl)-2-cyclobutylamino-ethanol was dissolved in isopropanol, and the solution was acidified to a pH of 5 with ethereal hydrochloric acid. The product crystallized out after addition of ether. The precipitated hydrochloride of the desired compound was recrystallized from isopropanol. M.p. 164°–166° C. (decomp.).

EXAMPLE 50

1-(4'-Amino-3'-fluoro-5'-iodo-phenyl)-2-isopropylamino-ethanol hydrochloride by method B 5.15 gm of 1-(4'-amino-3'-fluoro-phenyl)-2-isopropylamino-ethanol were dissolved in 300 ml of acetic acid; 80 gm of iodine and 4.0 gm of mercury-(II)-oxide were added to the solution, and the mixture was vigorously stirred for 2½ hours at room temperature. The solid matter was subsequently filtered off, the dark-brown filtrate was discolored with saturated sodium bisulfite solution and diluted to about 1 liter with water. The mixture was made alkaline with 10N sodium hydroxide while cooling, and was then extracted with chloroform. The chloroform phase was dried over sodium sulfate and evaporated to dryness in vacuo. The residue was dissolved in methanol, and the resulting solution was acidified to a pH of 4.5 with ethereal hydrochloric acid. The solution was evaporated to dryness in vacuo, and the solid residue was crystallized from absolute ethanol. M.p. 203°–205° C. (decomp.).

EXAMPLE 51

1-(4'-Amino-3'-cyano-phenyl)-2-cyclopropylamino-ethanol by method D 4 gm of 1-(4'-amino-3'-bromo-5'-cyano-phenyl)-2-cyclopropylamino-ethanol was dissolved in methanol, and the solution was hydrogenated at room temperature at a hydrogen pressure of 3 to 5 atmospheres after addition of 1 gm of palladized coal (10%). After termination of hydrogen absorption, the catalyst was suction-filtered off, the filtrate was evaporated to dryness in vacuo, and the residue was distributed between dilute sodium hydroxide and chloroform. After evaporation of the chloroform phase, 1-(4'-amino-3'-cyano-phenyl)-2-cyclopropylamino-ethanol was obtained as an oil, which was purified chromatographically on silicagel (eluant: chloroform:methanol = 9:1). The dihydrochloride, obtained by addition of ethereal hydrochloric acid, was recrystallized from isopropanol. M.p. 148°–151° C. (decomp.).

EXAMPLE 52

1-(4'-Amino-3'-bromo-5'-fluoro-phenyl)-2-cyclopentylamino-ethanol, m.p. of the hydrochloride: 167°–170° C. (decomp.), was prepared from 4'-amino-3'-bromo-2-cyclopentylamino-5'-fluoroacetophenone and sodium borohydride analogous to Example 49.

EXAMPLE 53

1-(4'-Amino-3'-bromo-5'-fluoro-phenyl)-2-cyclohexylamino-ethanol, m.p. of the hydrochloride: 191°–195° C. (decomp.), was prepared from 4'-amino-3'-bromo-2-cyclohexylamino-5'-fluoroacetophenone and sodium borohydride analogous to Example 49.

EXAMPLE 54

1-(4'-Amino-3'-fluoro-5'-iodo-phenyl)-2-cyclopropylamino-ethanol, m.p. of the hydrochloride: 199°–201° C. (decomp.), was prepared from 4'-amino-2-cyclopropylamino-3'-fluoro-5'-iodo-acetophenone and sodium borohydride analogous to Example 49.

EXAMPLE 55

1-(4'-Amino-3'-fluoro-5'-iodo-phenyl)-2-isopropylamino-ethanol, m.p. of the hydrochloride: 203°–205° C. (decomp.), was prepared from 4'-amino-3'-fluoro-2-isopropylamino-5'-iodo-acetophenone and sodium borohydride analogous to Example 49.

EXAMPLE 56

1-(4'-Amino-3'-fluoro-5'-iodo-phenyl)-2-cyclobutylamino-ethanol, m.p. of the hydrochloride: 197°–199° C. (decomp.), was prepared from 4'-amino-2-cyclobutylamino-3'-fluoro-5'-iodo-acetophenone analogous to Example 49.

EXAMPLE 57

1-(4'-Amino-3'-fluoro-5'-iodo-phenyl)-2-tert.butylamino-ethanol, m.p. of the hydrochloride: 207°–209° C. (decomp.), was prepared from 4'-amino-2-tert.butylamino-3'-fluoro-5'-iodo-acetophenone analogous to Example 49.

EXAMPLE 58

1-(4'-Amino-3'-fluoro-5'-iodo-phenyl)-2-(hydroxy-tert.butylamino)-ethanol, m.p. of the hydrochloride: 200°–202° C. (decomp.), was prepared from 4'-amino-3'-fluoro-2-hydroxy-tert.butylamino)-5'-iodo-acetophenone analogous to Example 49.

EXAMPLE 59

1-(4'-Amino-3'-cyano-5'-fluoro-phenyl)-2-cyclopropylamino-ethanol, m.p. of the hydrochloride: 188°–190° C. (decomp.), was prepared from 4'-amino-3'-cyano-2-cyclopropylamino-5'-fluoroacetophenone analogous to Example 49.

EXAMPLE 60

1-(4'-Amino-3'-cyano-5'-fluoro-phenyl)-2-isopropylamino-ethanol, m.p. of the hydrochloride: 182°–184° C. (decomp.), was prepared from 4'-amino-3'-cyano-5'-fluoro-2-isopropylaminoacetophenone analogous to Example 49.

EXAMPLE 61

1-(4'-Amino-3'-cyano-5'-fluoro-phenyl)-2-cyclobutylamino-ethanol, m.p. of the hydrochloride: 222°–224° C. (decomp.), was prepared from 4'-amino-3'-cyano-2-cyclobutylamino-5'-fluoroacetophenone analogous to Example 49.

EXAMPLE 62

1-(4'-Amino-3'-cyano-5'-fluoro-phenyl)-2-tert.butylamino-ethanol, m.p. of the hydrochloride: 242°–243° C. (decomp.), was prepared from 4'-amino-2-tert.butylamino-3'-cyano-5'-fluoroacetophenone analogous to Example 49.

EXAMPLE 63

1-(4'-Amino-3'-cyano-5'-fluoro-phenyl)-2-cyclopentylamino-ethanol, m.p. of the hydrochloride: 184°–186° C. (decomp.), was prepared from 4'-amino-3'-cyano-2-cyclopentylamino-5'-fluoroacetophenone analogous to Example 49.

EXAMPLE 64

1-(4'-Amino-3'-cyano-5'-fluoro-phenyl)-2-tert.pentylamino-ethanol, m.p. of the hydrochloride: 172°–175° C. (decomp.)., was prepared from 4'-amino-3'-cyano-5'-fluoro-2-tert.pentylaminoacetophenone analogous to Example 49.

EXAMPLE 65

1-(4'-Amino-3'-trifluoromethyl-phenyl)-2-cyclopentylamino-ethanol, m.p. of the hydrochloride: 144°–145° C., was prepared from 1-(4'-amino-3'-bromo-5'-trifluoromethylphenyl)-2-cyclopentylamino-ethanol analogous to Example 51.

EXAMPLE 66

1-(4'-Amino-3'-chloro-5'-trifluoromethyl-phenyl)-2-cyclopentylamino-ethanol, m.p. of the hydrochloride: 188°–190° C. (decomp.), was prepared from 4'-amino-3'-chloro-2-cyclopentylamino-5'-trifluoromethyl-acetophenone analogous to Example 48.

EXAMPLE 67

1-(4'-Amino-3'-cyano-phenyl)-2-cyclobutylamino-ethanol, m.p. of the hydrobromide: >193° C. (decomp.), was prepared from 1-(4'-amino-3'-bromo-5'-cyano-phenyl)-2-cyclobutylamino-ethanol analogous to Example 51.

EXAMPLE 68

1-(4'-Amino-3'-cyano-phenyl)-2-cyclopentylamino-ethanol, m.p. 158°–160° C., was prepared from 1-(4'-amino-3'-bromo-5'-cyanophenyl)-2-cyclopentylamino-ethanol analogous to Example 51.

EXAMPLE 69

1-(4'-Amino-3'-cyano-phenyl)-2-tert.pentylamino-ethanol, m.p. 143° C., was prepared from 1-(4'-amino-3'-bromo-5'-cyano-phenyl)-2-tert.pentylamino-ethanol analogous to Example 51.

EXAMPLE 70

1-(4'-Amino-3'-chloro-5'-cyano-phenyl)-2-cyclopropylamino-ethanol, m.p. of the hydrochloride: 175°–177° C., was prepared from 4'-amino-3'-chloro-5'-cyano-2-cyclopropylamino-acetophenone analogous to Example 48.

EXAMPLE 71

1-(4'-Amino-3'-chloro-5'-cyano-phenyl)-2-propylamino-ethanol, m.p. of the hydrochloride: 187°–189° C., was prepared from 4'-amino-3'-chloro-5'-cyano-2-propylamino-acetophenone analogous to Example 48.

EXAMPLE 72

1-(4'-Amino-3'-chloro-5'-cyano-phenyl)-2-cyclobutylamino-ethanol, m.p. of the hydrochloride: 178°–180° C. (decomp.), was prepared from 4'-amino-3'-chloro-5'-cyano-2-cyclobutylaminoacetophenone analogous to Example 48.

EXAMPLE 73

1-(4'-Amino-3'-chloro-5'-cyano-phenyl)-2-sec.-butylamino-ethanol, m.p. of the dihydrochloride: 190°–191° C., was prepared from 4'-amino-2-sec.butylamino-3'-chloro-5'-cyano-acetophenone analogous to Example 48.

EXAMPLE 74

1-(4'-Amino-3'-chloro-5'-cyano-phenyl)-2-(hydroxy-tert.butylamino)-ethanol, m.p. of the hydrochloride: 228°–230° C. (decomp.), was prepared from 4'-amino-3'-chloro-5'-cyano-2-(hydroxy-tert.butylamino)-acetophenone analogous to Example 48.

EXAMPLE 75

1-(4'-Amino-3'-chloro-5'-cyano-phenyl)-2-cyclopentylamino-ethanol, m.p. of the hydrochloride: 138°–144° C., was prepared from 4'-amino-3'-chloro-5'-cyano-2-cyclopentylamino-acetophenone analogous to Example 48.

EXAMPLE 76

1-(4'-Amino-3'-chloro-5'-cyano-phenyl)-2-tert.pentylamino-ethanol, m.p. of the hydrochloride: 218°–220° C. (decomp.), was prepared from 4'-amino-3'-chloro-5'-cyano-2-tert.pentylaminoacetophenone analogous to Example 48.

EXAMPLE 77

1-(4'-Amino-3'-chloro-5'-cyano-phenyl)-2-[1''-(3,4-methylenedioxy-phenyl)-2''-propylamino]-ethanol, m.p. of the hydrochloride: 189°–192° C., was prepared from 4'-amino-3'-chloro-5'-cyano-2-[1''-(3,4-methylenedioxy-phenyl)-2''-propylamino]acetophenone analogous to Example 48.

EXAMPLE 78

1-(4'-Amino-3'-bromo-5'-cyano-phenyl)-2-cyclobutylamino-ethanol, m.p. of the hydrochloride: 215°–216° C. (decomp.), was prepared from 4'-amino-3'-bromo-5'-cyano-2-cyclobutylaminoacetophenone analogous to Example 48.

EXAMPLE 79

1-(4'-Amino-3'-bromo-5'-cyano-phenyl)-2-(hydroxy-tert.butylamino)-ethanol, m.p. of the hydrochloride: 221°–222° C., was prepared from 4'-amino-3'-bromo-5'-cyano-2-(hydroxy-tert.butylamino)-acetophenone analogous to Example 48.

EXAMPLE 80

1-(4'-Amino-3'-bromo-5'-cyano-phenyl)-2-cyclopentylamino-ethanol, m.p. of the hydrochloride: 177° C., was prepared from 4'-amino-3'-bromo-5'-cyano-2-cyclopentylamino-acetophenone analogous to Example 48.

EXAMPLE 81

1-(4'-Amino-3'-bromo-5'-cyano-phenyl)-2-tert.pentylamino-ethanol, m.p. of the hydrochloride: 202°–204° C. (decomp.), was prepared from 4'-amino-3'-bromo-5'-cyano-2-tert.pentylaminoacetophenone analogous to Example 48.

EXAMPLE 82

1-(4'-Amino-3',5'-dicyano-phenyl)-2-isopropylamino-ethanol, m.p. of the hydrochloride: 224°–226° C. (decomp.), was prepared from 4'-amino-3',5'-dicyano-2-isopropylamino-acetophenone analogous to Example 48.

EXAMPLE 83

1-(4'-Amino-3',5'-dicyano-phenyl)-2-cyclobutylamino-ethanol, m.p. of the hydrochloride: 258° C. (decomp.), was prepared from 4'-amino-2-cyclobutylamino-3',5'-dicyano-acetophenone analogous to Example 48.

EXAMPLE 84

1-(4'-Amino-3',5'-dicyano-phenyl)-2-sec.butylamino-ethanol, m.p. of the hydrochloride: 197°–199° C., was prepared from 4'-amino-2-sec.butylamino-3',5'-dicyano-acetophenone analogous to Example 48.

EXAMPLE 85

1-(4'-Amino-3',5'-dicyano-phenyl)-2-tert.butylamino-ethanol, m.p. of the hydrochloride: 251°–253° C. (decomp.), was prepared from 4'-amino-2-tert.butylamino-3',5'-dicyano-acetophenone analogous to Example 48.

EXAMPLE 86

1-(4'-Amino-3',5'-dicyano-phenyl)-2-(hydroxy-tert.butylamino)-ethanol, m.p. of the hydrochloride: 240°–241° C. (decomp.), was prepared from 4'-amino-3',5'-dicyano-2-(hydroxy-tert.butylamino)-acetophenone analogous to Example 48.

EXAMPLE 87

1-(4'-Amino-3',5'-dicyano-phenyl)-2-cyclopentylamino-ethanol, m.p. of the hydrochloride: 214°–216° C., was prepared from 4'-amino-2-cyclopentylamino-3',5'-dicyano-acetophenone analogous to Example 48.

EXAMPLE 88

1-(4'-Amino-3',5'-dicyano-phenyl)-2-tert.pentylamino-ethanol, m.p. of the hydrochloride: 231°–233° C. (decomp.), was prepared from 4'-amino-3',5'-dicyano-2-tert.pentylamino-acetophenone analogous to Example 48.

EXAMPLE 89

1-(4'-Amino-3',5'-dicyano-phenyl)-2-[1'''-(3,4-methylenedioxyphenyl)-2''-propylamino]-ethanol, m.p. of the hydrochloride: 219°–222° C. (decomp.), was prepared from 4'-amino-3',5'-dicyano-2-[1'''-(3,4-methylenedioxy-phenyl)-2''-propylamino]-acetophenone analogous to Example 48.

EXAMPLE 90

1-(4'-Amino-3'-chloro-5'-nitro-phenyl)-2-tert.butylamino-ethanol, m.p. 148°–149° C., was prepared from 4'-amino-2-tert.butylamino-3'-chloro-5'-nitro-acetophenone analogous to Example 48.

EXAMPLE 91

1-(4'-Amino-3'-bromo-5'-nitro-phenyl)-2-tert.butylamino-ethanol, m.p. 151°–152° C., was prepared from 4'-amino-3'-bromo-2-tert.butylamino-5'-nitro-acetophenone analogous to Example 48.

EXAMPLE 92

Isolation of
l-1-(4'-amino-3'-fluoro-phenyl)-2-tert.butylamino-ethanol and
d-1-(4'-amino-3'-fluoro-phenyl)-2-tert.butylamino-ethanol (a) l-1-(4'-Acetylamino-3'-fluoro-phenyl)-2-(N-benzyl-N-tert.butyl)-amino-O-(N-carbobenzoxy-L-alanyl)-ethanol and d-1-(4'-acetylamino-3'-fluoro-phenyl)-2-(N-benzyl-N-tert.butyl)-amino-O-(N-carbobenzoxy-L-alanyl)-ethanol To a solution of 15 gm of N-carbobenzoxy-L-alanin in 300 ml of absolute tetrahydrofuran 14.5 gm of N,N'-carbonyldiimidazole were added, and the mixture was stirred for 3 hours at room temperature. Subsequently, a solution of 10 gm of d,l-1-(4'-acetylamino-3'-fluoro-phenyl)-2-(N-benzyl-N-tert.butyl)-amino-ethanol in 200 ml of absolute tetrahydrofuran and a small piece of sodium were added, and the mixture was stirred for 12 days at room temperature and was then evaporated to dryness in vacuo. The residue was distributed between chloroform and water. The chloroform layer was dried over sodium sulfate and evaporated to dryness in vacuo. The two diastereomeric esters thus obtained in the mixture show different $R_f$-values in the thin-layer chromatogram (silicagel G, Merck; chloroform:acetone = 10:1). The above evaporation residue was purified on a silicagel chromatography column without separating the diastereomeric esters (500 gm of silicagel; eluant: chloroform:acetone = 10:1).

The eluate fractions containing the desired substance were evaporated to dryness in vacuo, and the residue was recrystallized from ether, yielding l-1-(4'-acetylamino-3'-fluoro-phenyl)-2-(N-benzyl-N-tert.butyl)-amino-O-(N-carbobenzoxy-L-alanyl)-ethanol as colorless crystals. $[\alpha]_{364}^{20} = -101°$ ($c = 2.0$; methanol); $R_f$-value = 0.27. The mother liquor was evaporated to dryness in vacuo. The diastereomeric ester with the larger $R_f$-value ($R_f = 0.33$) was isolated in a chromatography column (100 gm of silicagel; eluant: chloroform:acetone = 20:1). d-1-(4'-acetylamino-3'-fluoro-phenyl)-2-(N-benzyl-N-tert.butylamino)-O-(N-carbobenzoxy-L-alanyl)-ethanol was thus obtained as a colorless oil. $[\alpha]_{364}^{20} = -65°$ ($c = 2.0$; methanol); $R_f$-value = 0.33.

(b) l-1-(4'-Amino-3'-fluoro-phenyl)-2-tert.butylamino-ethanol 2 gm of l-1-(4'-acetylamino-3'-fluoro-phenyl)-2-(N-benzyl-N-tert.butylamino)-O-(N-carbobenzoxy-L-alanyl)-ethanol were dissolved in 60 ml of ethanol. 20 ml of 5N sodium hydroxide were added, and the solution was refluxed for 4 hours. After cooling, the solution was distributed between chloroform and water, and the aqueous layer was extracted four times with chloroform. The combined chloroform extracts were dried over sodium sulfate and evaporated to dryness in vacuo. The residue, consisting of 1-1-(4'-amino-3'-fluoro-phenyl)-2-(N-benzyl-N-ter.butylamino)-ethanol, was dissolved in 50 ml of methanol, and the solution was acidified to a pH of 6 with ethereal hydrochloric acid; 0.2 gm of palladized coal (10%) were added, and the mixture was hydrogenated in a Parr-apparatus at room temperature and at a pressure of 5 atmospheres until no more hydrogen was being absorbed. The catalyst was suction-filtered off, the filtrate was evaporated to dryness in vacuo, and the solid residue, consisting of 1-1-(4'-amino-3'-fluoro-phenyl)-2-tert.butylamino-ethanol hydrochloride, was crystallized from isopropanol by addition of ether. M.p. 199°–200° C. (decomp.), $[\alpha]_{364}^{20} = -123.3°$ ($c = 1.0$; methanol).

(c) d-1-(4'-Amino-3'-fluoro-phenyl)-2-tert.butylaminoethanol

The oily d-1-(4'-acetylamino-3'-fluoro-phenyl)-2-(N-benzyl-N-tert.butylamino)-O-(N-carbobenzoxy-L-alanyl)-ethanol obtained in step a) was dissolved in 30 ml of ethanol. 10 ml of 5N sodium hydroxide were added, and the solution was refluxed for 4 hours. After cooling, the reaction solution was distributed between chloroform and water, and the aqueous phase was extracted four times with chloroform. The combined chloroform extracts were dried over sodium sulfate and evaporated to dryness in vacuo. The residue, consisting of d-1-(4'-amino-3'-fluoro-phenyl)-2-(N-benzyl-N-tert.butylamino)-ethanol, was dissolved in 25 ml of methanol, the solution was acidified to a pH of 6 with ethereal hydrochloric acid, 0.1 gm of palladized coal (10%) were added, and the reaction mixture was hydrogenated in a Parr-apparatus at room temperature and at a pressure of 5 atmospheres until no more hydrogen was being absorbed. The catalyst was then suction-filtered off, the filtrate was evaporated to dryness in vacuo, and the solid residue, consisting of d-1-(4'-amino-3'-fluoro-phenyl)-2-tert.butylamino-ethanol hydrochloride, was crystallized from isopropanol by addition of ether. M.p. 198°–200° C. (decomp.). $[\alpha]_{364}^{20} = +124.4°$ ($c = 1.142$; methanol).

EXAMPLE 93

Isolation of
d-1-(4'-amino-3'-chloro-5-trifluoromethyl-phenyl)-2-tert.butylamino-ethanol and
1-1-(4'-amino-3'-chloro-5'-trifluoromethyl-phenyl)-2-tert.butylamino-ethanol (a) d,1-1-(4'-Amino-3'-chloro-5'-trifluoromethyl-phenyl)-2-tert.butylamino-O-[(−)-menthoxy-carbonyl]-ethanol 56.6 ml of a 0.5 molar solution of chloroformic acid-(−)-menthylester in toluene were added dropwise, while stirring, to a solution of 8.8 gm of d,1-1-(4'-amino-3'-chloro-5'-trifluoromethyl-phenyl)-2-tert.butylamino-ethanol in 50 ml of pyridine at 20° C. After two hours the reaction solution was evaporated to dryness in vacuo. The oily residue was triturated with water and subsequently dissolved in ether after the aqueous phase had been decanted. The ethereal solution was successively washed with water, 2N ammonia (whereby a precipitate formed between the layers was dissolved) and again with water. The ethereal solution was dried with magnesium sulfate and then adjusted to a pH of 6 with 4N isopropanolic hydrochloric acid. A mixture of the hydrochlorides of the above-named diastereomeric isomers crystallied out. The crystalline reaction product was suction-filtered off and washed with ether.

In the thin-layer chromatogram on silicagel G (Merck) with butyl acetate:cyclohexane = 9:1 the crystals showed two spots of the same concentration with the approximate $R_f$-values of 0.45 and 0.55, respectively.

(b) Separation of d- and l-1-(4'-amino-3'-chloro-5'-trifluoromethyl-phenyl)-2-tert.butylamino-O-[(−)-menthoxy-cabonyl]-ethanol 3.0 gm of the mixture of the hydrochlorides of d- and 1-1-(4'-amino-3'-chloro-trifluoromethyl-phenyl)-2-tert.butylamino-O-[(−)-menthoxy-carbonyl]-ethanol obtained in step a) were suspended in a small quantity of water, the suspension was covered with ether, 5.0 ml of 2N ammonia were added, and the mixture was shaken until everything had dissolved. The ethereal phase was separated, washed with water, dried over magnesium sulfate and evaporated in vacuo. The oily residue was chromatographed on a silicagel column (6.5 cm in diameter; 107 cm in length; 2.2 kg of silicagel) with a mixture of butyl acetate:cyclohexane = 19:1 (flow speed 120 ml/hour). The fractions containing the desired pure substance of $R_f$-value 0.55 were combined, and the solvent was removed in vacuo, yielding d-1-(4'-amino-3'-chloro-5'-trifluoromethyl-phenyl)-2-tert.butylamino-O-[(−)-menthoxy-carbonyl]-ethanol which was crystallized from petroleum ether (boiling point: 40°–60° C.). M.p. 95.5°–96.5° C. $[\alpha]_{364}^{20} = +74.1°$ ($c = 1.0$; chloroform).

The fractions containing mixtures of the diastereomeric isomers, and which may be added to a further chromatographic separation, were eliminated. The fractions containing almost pure substance with the $R_f$-value of 0.45, were combined and evaporated in vacuo. The residue was recrystallized once from petroleum ether yielding chromtographically pure 1-1-(4'-amino-3'-chloro-5'-trifluoromethyl-phenyl)-2-tert.butylamino-O-[(−)-menthoxy-carbonyl]-ethanol, m.p. 102°–104° C. $[\alpha]_{364}^{20} = -273.5°$ ($c = 1.0$; chloroform).

(c) d-1-(4'-Amino-3'-chloro-5'-trifluoromethyl-phenyl)-2-tert.butylamino-ethanol 1.6 gm of d-1-(4'-amino-3'-chloro-5'-trifluoromethyl-phenyl)-2-tert.butylamino-O-[(−)-menthoxy-carbonyl]-ethanol were dissolved in 16 ml of methanol, and the solution was allowed to stand for 65 hours at about 20° C. The reaction mixture was then evaporated in vacuo, and the residue was purified by column chromatography (silicagel; chloroform: methanol:concentrated ammonia = 90:10:1). The fractions containing the desired substance were combined and evaporated in vacuo. The residue was dissolved in ethyl acetate, and the calculated quantity of isopropanolic 4N hydrochloric acid was added, whereupon the hydrochloride of the above-named compound crystallized out. M.p. >194° C. slow decomposition. $[\alpha]_{364}^{20} = +154.9°$ ($c = 1.0$; methanol).

(d) 1-1-(4'-Amino-3'-chloro-5'-trifluoromethyl-phenyl)-2-tert.butylamino-ethanol was prepared from 1.58 gm of 1-1-(4'-amino-3'-chloro-5'-trifluoromethyl-phenyl)-2-tert.butylamino-O-[(−)-menthoxy-carbonyl]-ethanol by solvolysis with methanol and chromatographic purification analogous to step c) for the enantiomeric compound. M.p. of the hydrochloride: >194° C. slow decomposition. $[\alpha]_{364}^{20} = -154.8°$ ($c = 1.0$; methanol).

EXAMPLE 94

Isolation of
d-1-(4'-amino-3'-bromo-5'-fluoro-phenyl)-2-tert-.butylamino-ethanol and
l-1-(4'-amino-3'-bromo-5'-fluoro-phenyl)-2-tert-.butylamino-ethanol 205 gm of d,l-1-(4'-amino-3'-bromo-5'-fluoro-phenyl)-2-tert.butylamino-ethanol and 118 gm of dibenzoyl-D-tartaric acid were dissolved in 2.5 liters of hot ethanol, and the solution was filtered and left standing for one day at room temperature for crystallization. The crude product thus obtained was recrystallized six times from methanol-ether, yielding pure d-[1-(4'-amino-3'-bromo-5'-fluoro-phenyl)-2-tert.butylamino-ethanol]-dibenzoyl-D-tartrate, m.p. 206°–208° C. (decomp.). $[\alpha]_{364}^{20} = +332.9°$ ($c = 2.0$; methanol).

The salt thus obtained was dissolved in methanol and concentrated ammonia while heating, and the base was caused to crystallize by addition of water. The base was dissolved in absolute ethanol, the solution was neutralized with absolute ethanolic hydrochloric acid, and the crystallization of d-1-(4'-amino-3'-bromo-5'-fluoro-phenyl)-2-tert.butylamino-ethanol hydrochloride was completed by addition of ether. M.p. 234°–235° C. (decomp.). $[\alpha]_{364}^{20} = +132.0°$ ($c = 2.0$; methanol).

The mother liquor from the precipitation of d-[1-(4'-amino-3'-bromo-5'-fluoro-phenyl)-2-tert.butylamino-ethanol]-dibenzoyl-D-tartrate and that from the first recrystallization were combined, evaporated to a smaller volume, and the base was precipitated by addition of concentrated ammonia and water. 140 gm of 1-(4'-amino-3'-bromo-5'-fluoro-phenyl)-2-tert-.butylamino-ethanol (1-form concentrated) thus obtained were dissolved in 1.8 liters of absolute ethanol, and a solution of 82 gm of dibenzoyl-L-tartaric acid in 500 ml of absolute ethanol was added; the mixture was evaporated to a volume of 1 liter and left standing for three days at room temperature for crystallization. The obtained product was recrystallized six times from methanol/ether, yielding l-[1-4'-amino-3'-bromo-5'-fluoro-phenyl)-2-tert.butylamino-ethanol]-dibenzoyl-L-tartrate in pure form. M.p. 204°–206° C. (decomp.). $[\alpha]_{364}^{20} = -330.2°$ ($c = 2.0$; methanol).

The salt was dissolved in methanol and concentrated ammonia while heating, the base was precipitated by addition of water and was dissolved in absolute ethanol, the solution was neutralized with absolute ethanolic hydrochloric acid, and 1-1-(4'-amino-3'-bromo-5'-fluoro-phenyl)-2-tert.butylamino-ethanol hydrochloride was caused to crystallize out by addition of ether. M.p 218°–220° C. (decomp.). $[\alpha]_{364}^{20} = -133.9°$ ($c = 2.0$; methanol).

EXAMPLE 95 d-1-(4'-Amino-3'-chloro-5'-fluoro-phenyl)-2-tert-.butylamino-ethanol, m.p. of the hydrochloride: 210°–211° C. (decomp.), $[\alpha]_{364}^{20} = +139.7°$ ($c = 2.0$; methanol), was prepared from d,l-1-(4'-amino-3'-chloro-5'-fluoro-phenyl)-2-tert-.butylamino-ethanol by fractional crystallization of the dibenzoyl-D-tartrate analogous to Example 94.

l-1-(4'-Amino-3'-chloro-5'-fluoro-phenyl)-2-tert-.butylamino-ethanol, m.p. of the hydrochloride: 209°–210° C. (decomp.), $[\alpha]_{364}^{20} = -139.2°$ ($c = 2.0$; methanol), was prepared from d,l-1-(4'-amino-3'-chloro-5'-fluoro-phenyl)-2-tert-.butylamino-ethanol by fractional crystallization of the dibenzoyl-L-tartrate analogous to Example 94.

EXAMPLE 96 d-1-(4'-Amino-3'-chloro-5'-cyano-phenyl)-2-tert-.butylamino-ethanol, m.p. of the hydrochloride: 197°–199° C. (decomp.), $[\alpha]_{364}^{20} = +59.9°$ ($c = 2.0$; methanol), was prepared from d,l-1-(4'-amino-3'-chloro-5'-cyano-phenyl)-2-tert-.butylamino-ethanol by fractional crystallization of the dibenzoyl-D-tartrate analogous to Example 94.

l-1-(4'-Amino-3'-chloro-5'-cyano-phenyl)-2-tert-.butylamino-ethanol, m.p. of the hydrochloride: 199°–202° C. (decomp.), $[\alpha]_{364}^{20} = -59.85°$ ($c = 2.0$; methanol), was prepared from d,l-1-(4'-amino-3'-chloro-5'-cyano-phenyl)-2-tert-.butylamino-ethanol by fractional crystallization of the dibenzoyl-L-tartrate analogous to Example 94.

EXAMPLE 97 d-1-(4'-Amino-3'-chloro-5'-fluoro-phenyl)-2-tert-.butylamino-ethanol 0.26 gm of d-1-(4'-amino-3'-fluoro-phenyl)-2-tert-.butylamino-ethanol hydrochloride and 0.2 ml of pyridine were dissolved in 30 ml of tetrahydrofuran, and the solution was cooled to 0° C. 0.3 gm of iodobenzene dichloride were added, the mixture was held at 0° C. for 2 hours, and then 0.1 gm of iodobenzene dichloride was added again. After standing for 20 hours at about 4° C. the solution was evaporated, and the residue was distributed between ethyl acetate and water. The aqueous phase was made alkaline with 2N ammonia and was then extracted again with ethyl acetate. The organic phase was washed with water, dried and evaporated to dryness in vacuo. The residue was dissolved in absolute ethanol, the solution was neutralized with ethanolic hydrochloric acid, and the hydrochloride of the above-named compound was caused to crystallize by addition of ether. M.p. 210°–211° C. (decomp.). $[\alpha]_{364}^{20} = +139.6°$ ($c = 2.0$; methanol).

EXAMPLE 98 d-1-(4'-Amino-3'-bromo-5'-fluoro-phenyl)-2-tert-.butylamino-ethanol 0.26 gm of d-1-(4'-amino-3'-fluoro-phenyl)-2-tert-.butylamino-ethanol hydrochloride was dissolved in 30 ml of 50% acetic acid, and a solution of 0.16 gm of bromine in 5 ml of acetic acid and 1 ml of water was added at 0°–5° C. After 15 minutes of standing, the reaction mixture was evaporated, the residue was dissolved in water, and the aqueous solution was made alkaline with 2N ammonia and was then extracted with chloroform. The chloroform extract was dried with sodium sulfate and evaporated to dryness in vacuo. The residue was converted into the hydrochloride of the above-named compound by dissolving it in ethanol, neutralizing the solution with ethanolic hydrochloric acid and adding ether. M.p. 234°–235° C. (decomp.). $[\alpha]_{364}^{20} = +132.0°$ ($c = 2.0$; methanol).

EXAMPLE 99

1-(4'-Amino-3'-cyano-phenyl)-2-cyclobutylamino-ethanol, m.p. of the hydrobromide: >193° C. (decomp.), was prepared from 4'-amino-3'-cyano-2-cyclobutylamino-acetophenone hydrochloride analogous to Example 1.

In analogous manner, the following compounds of the formula I were also prepared:
(a) 1-(4'-Amino-3'-cyano-phenyl)-2-tert.pentylamino-ethanol, m.p. 143° C.
(b) 1-(4'-Amino-3'-trifluoromethyl-phenyl)-2-tert.butylamino-ethanol, m.p. of the hydrochloride: 172°–174° C. (decomp.).
(c) 1-(4'-Amino-3'-trifluoromethyl-phenyl)-2-tert.pentylamino-ethanol, m.p. of the hydrobromide: 174°–175° C. (decomp.).

EXAMPLE 100

1-(4'-Amino-3'-chloro-5'-fluoro-phenyl)-2-isopropylamino ethanol, m.p. of the hydrochloride: 152°–154° C. (decomp.), was prepared from 1-(4'-amino-3'-fluoro-phenyl)-2-isopropylamino-ethanol hydrochloride and chlorine analogous to Example 98.

The following compounds of the formula I were also prepared analogous to Examples 3 or 50:
(a) 1-(4'-Amino-3'-chloro-5'-fluoro-phenyl)-2-cyclopropylamino-ethanol hydrochloride, m.p. 175°–177° C. (decomp.).
(b) 1-(4'-Amino-3'-chloro-5'-fluoro-phenyl)-2-tert.butylamino-ethanol hydrochloride, m.p. 206°–208° C. (decomp.).
(c) 1-(4'-Amino-3'-chloro-5'-fluoro-phenyl)-2-tert.pentylamino-ethanol hydrochloride, m.p. 187°–188° C. (decomp.).
(d) 1-(4'-Amino-3'-bromo-5'-fluoro-phenyl)-2-isopropylamino-ethanol hydrochloride, m.p. 171°–173° C. (decomp.).
(e) 1-(4'-Amino-3'-bromo-5'-fluoro-phenyl)-2-tert.butylamino-ethanol hydrochloride, m.p. 207°–208° C. (decomp.).
(f) 1-(4'-Amino-3'-bromo-5'-fluoro-phenyl)-2-cyclobutylamino-ethanol hydrochloride, m.p. 164°–166° C. (decomp.).
(g) 1-(4'-Amino-3'-fluoro-5'-iodo-phenyl)-2-cyclopropylamino-ethanol hydrochloride, m.p. 199°–201° C. (decomp.).
(h) 1-(4'-Amino-3'-chloro-5'-cyano-phenyl)-2-propylamino-ethanol hydrochloride, m.p. 187°–189° C.
(i) 1-(4'-Amino-3'-chloro-5'-cyano-phenyl)-2-sec.-butylamino-ethanol dihydrochloride, m.p. 190°–191° C.
(j) 1-(4'-Amino-3'-chloro-5'-cyano-phenyl)-2-tert.butylamino-ethanol, m.p. 125°–133° C.
(k) 1-(4'-Amino-3'-chloro-5'-cyano-phenyl)-2-(hydroxy-tert.butylamino)-ethanol hydrochloride, m.p. 228°–230° L C. (decomp.).
(l) 1-(4'-Amino-3'-chloro-5'-cyano-phenyl)-2-tert.pentylamino-ethanol hydrochloride, m.p. 218°–220° C. (decomp.).
(m) 1-(4'-Amino-3'-chloro-5'-cyano-phenyl)-2-cyclopentylamino-ethanol hydrochloride, m.p. 138°–144° C.
(n) 1-(4'-Amino-3'-chloro-5'-cyano-phenyl)-2-[1'''-(3,4-methylenedioxy-phenyl)-2'''-propylamino]-ethanol hydrochloride, m.p. 189°–192° C.
(o) 1-(4'-Amino-3'-bromo-5'-cyano-phenyl)-2-isopropylamino-ethanol hydrochloride, m.p. 186°–189° C.
(p) 1-(4'-Amino-3'-bromo-5'-cyano-phenyl)-2-tert.butylamino-ethanol hydrochloride, m.p. 213°–215° C.
(q) 1-(4'-Amino-3'-bromo-5'-cyano-phenyl)-2-cyclobutylamino-ethanol hydrochloride, m.p. 215°–216° C. (decomp.).
(r) 1-(4'-Amino-3'-chloro-5'-trifluoromethyl-phenyl)-2-isopropylamino-ethanol, m.p. 104°–106° C.
(s) 1-(4'-Amino-3'-chloro-5'-trifluoromethyl-phenyl)-2-tert.butylamino-ethanol hydrochloride, m.p. 205°–207° C. (decomp.).
(t) 1-(4'-Amino-3'-chloro-5'-trifluoromethyl-phenyl)-2-cyclobutylamino-ethanol hydrochloride, m.p. 177°–178° C.
(u) 1-(4'-Amino-3'-chloro-5'-trifluoromethyl-phenyl)-2-tert.pentylamino-ethanol hydrochloride, m.p. 176°–178° C. (decomp.).
(v) 1-(4'-Amino-3'-bromo-5'-trifluoromethyl-phenyl)-2-isopropylamino-ethanol hydrochloride, m.p. 177°–179° C. (decomp.).
(w) 1-(4'-Amino-3'-chloro-5'-nitro-phenyl)-2-tert.butylamino-ethanol, m.p. 148°–149° C.
(x) 1-(4'-Amino-3'-bromo-5'-nitro-phenyl)-2-tert.butylamino-ethanol, m.p. 151°–152° C.

EXAMPLE 101

1-(4'-Amino-3'-chloro-5'-fluoro-phenyl)-2-isopropylamino-ethanol, m.p. of the hydrochloride: 152°–154° C. (decomp.), was prepared from 1-(4'-acetylamino-3'-chloro-5'-fluoro-phenyl)-2-isopropylamino-ethanol hydrochloride analogous to Example 4, or from 1-(4'-amino-3'-chloro-5'-fluoro-phenyl)-2-(N-benzyl-N-isopropylamino-ethanol analogous to Example 5.

The following compounds of the formula I were also prepared in analogous manner:
(a) 1-(4'-Amino-3'-chloro-5'-fluoro-phenyl)-2-cyclopropylamino-ethanol hydrochloride, m.p. 175°–177° C. (decomp.).
(b) 1-(4'-Amino-3'-chloro-5'-fluoro-phenyl)-2-tert.pentylamino-ethanol hydrochloride, m.p. 187°–188° C. (decomp.).
(c) 1-(4'-Amino-3'-bromo-5'-fluoro-phenyl)-2-isopropylamino-ethanol hydrochloride, m.p. 171°–173° C. (decomp.).
(d) 1-(4'-Amino-3'-bromo-5'-fluoro-phenyl)-2-tert.butylamino-ethanol hydrochloride, m.p. 207°–208° C. (decomp.).
(e) 1-(4'-Amino-3'-bromo-5'-fluoro-phenyl)-2-cyclobutylamino-ethanol hydrochloride, m.p. 164°–166° C. (decomp.).
(f) 1-(4'-Amino-3'-fluoro-5'-iodo-phenyl)-2-cyclopropylamino-ethanol hydrochloride, m.p. 199°–201° C. (decomp.).

(g) 1-(4'-Amino-3'-trifluoromethyl-phenyl)-2-tert.pentylamino-ethanol hydrobromide, m.p. 174°–175° C. (decomp.).

(h) 1-(4'-Amino-3'-chloro-5'-trifluoromethyl-phenyl)-2-isopropylamino-ethanol, m.p. 104°–106° C.

(i) 1-(4'-Amino-3'-chloro-5'-trifluoromethyl-phenyl)-2-tert.butylamino-ethanol hydrochloride, m.p. 205°–207° C. (decomp.).

(j) 1-(4'-Amino-3'-chloro-5'-trifluoromethyl-phenyl)-2-cyclobutylamino-ethanol hydrochloride, m.p. 177°–178° C.

(k) 1-(4'-Amino-3'-chloro-5'-trifluoromethyl-phenyl)-2-tert.pentylamino-ethanol hydrochloride, m.p. 176°–178° C. (decomp.).

(l) 1-(4'-Amino-3'-bromo-5'-trifluoromethyl-phenyl)-2-isopropylamino-ethanol hydrochloride, m.p. 177°–179° C. (decomp.).

EXAMPLE 102

1-(4'-Amino-3'-chloro-5'-nitro-phenyl)-2-tert.butylamino-ethanol, m.p. 148°–149° C., was prepared from 1-(4'-acetylamino-3'-chloro-5'-nitro-phenyl)-2-tert.butylamino-ethanol hydrochloride analogous to Example 4.

The following compound was prepared in analogous manner:

(a) 1-(4'-Amino-3'-bromo-5'-nitro-phenyl)-2-tert.butylamino-ethanol, m.p. 151°–152° C.

EXAMPLE 104

1-(4'-Amino-3'-fluoro-phenyl)-2-tert.butylamino-ethanol, m.p. of the hydrochloride: 196°–197° C. (decomp.), was prepared from 1-(4'-amino-3'-bromo-5'-fluoro-phenyl)-2-tert.butylamino-ethanol analogous to Example 7.

The following compound was prepared in analogous manner:

(a) 1-(4'-Amino-3'-trifluoromethyl-phenyl)-2-tert.butylamino-ethanol, m.p. of the hydrochloride: 172°–174° C. (decomp.).

EXAMPLE 105

1-(4'-Amino-3'-chloro-5'-trifluoromethyl-phenyl)-2-tert.butylamino-ethanol and its hydrochloride 3.4 gm of 1-(4'-amino-3'-chloro-5'-trifluoromethyl-phenyl)-2-bromo-ethanol were dissolved in 25 ml of tert.butylamine, and the solution was allowed to stand for 20 hours at room temperature. Thereafter, the excess tert.butylamine was removed in vacuo, and the residue was dissolved in ether. The ethereal solution was washed with water, dried over magnesium sulfate and evaporated in vacuo. The evaporation residue was chromatographically purified on a silicagel column (chloroform:methanol:concentrated ammonia = 90:10:1). The combined fractions containing the desired substance were evaporated to dryness in vacuo. The residue was dissolved in ether, and the solution was adjusted to a pH of 4 with isopropanolic hydrochloric acid, whereupon 1-(4'-amino-3'-chloro-5'-trifluoromethyl-phenyl)-2-tert.butylamino-ethanol hydrochloride crystallized out, which was suction-filtered off and washed with ether. It melted at 205°–207° C. (decomp.).

EXAMPLE 106

1-(4'-Amino-3'-chloro-5'-trifluoromethyl-phenyl)-2-tert.butylamino-ethanol, m.p. of the hydrochloride: 205°–207° C. (decomp.), was prepared from 1-(4'-amino-3'-chloro-5'-trifluoromethyl-phenyl)-2-(p-toluenesulfonyloxy)-ethanol and an excess of tert.butylamine analogous to Example 105.

The following compounds were also prepared in a manner analogous to Example 105:

(a) 1-(4'-Amino-3'-fluoro-phenyl)-2-tert.butylamino-ethanol hydrochloride, m.p. 196°–197° C. (decomp.).

(b) 1-(4'-Amino-3'-chloro-5'-fluoro-phenyl)-2-isopropylamino-ethanol hydrochloride, m.p. 152°–154° C. (decomp.).

(c) 1-(4'-Amino-3'-chloro-5'-fluoro-phenyl)-2-cyclopropylamino-ethanol hydrochloride, m.p. 175°–177° C. (decomp.).

(d) 1-(4'-Amino-3'-chloro-5'-fluoro-phenyl)-2-tert.butylamino-ethanol hydrochloride, m.p. 206°–208° C. (decomp.).

(e) 1-(4'-Amino-3'-chloro-5'-fluoro-phenyl)-2-tert.pentylamino-ethanol hydrochloride, m.p. 187°–188° C. (decomp.).

(f) 1-(4'-Amino-3'-bromo-5'-fluoro-phenyl)-2-isopropylamino-ethanol hydrochloride, m.p. 171°–173° C. (decomp.).

(g) 1-(4'-Amino-3'-bromo-5'-fluoro-phenyl)-2-tert.butylamino-ethanol hydrochloride, m.p. 207°–208° C. (decomp.).

(h) 1-(4'-Amino-3'-bromo-5'-fluoro-phenyl)-2-cyclobutylamino-ethanol hydrochloride, m.p. 164°–166° C. (decomp.).

(i) 1-(4'-Amino-3'-fluoro-5'-iodo-phenyl)-2-cyclopropylamino-ethanol hydrochloride, m.p. 199°–201° C. (decomp.).

(j) 1-(4'-Amino-3'-cyano-5'-fluoro-phenyl)-2-isopropylamino-ethanol hydrochloride, m.p. 182°–184° C. (decomp.).

(k) 1-(4'-Amino-3'-cyano-5'-fluoro-phenyl)-2-tert.butylamino-ethanol hydrochloride, m.p. 242°–243° C. (decomp.).

(l) 1-(4'-Amino-3'-cyano-phenyl)-2-cyclobutylamino-ethanol hydrobromide, m.p. > 193° C. (decomp.).

(m) 1-(4'-Amino-3'-cyano-phenyl)-2-tert.pentylamino-ethanol, m.p. 143° C.

(n) 1-(4'-Amino-3'-chloro-5'-cyano-phenyl)-2-propylamino-ethanol hydrochloride, m.p. 187°–189° C.

(o) 1-(4'-Amino-3'-chloro-5'-cyano-phenyl)-2-sec.-butylamino-ethanol dihydrochloride, m.p. 190°–191° C.

(p) 1-(4'-Amino-3'-chloro-5'-cyano-phenyl)-2-tert.butylamino-ethanol, m.p. 125°–133° C.

(q) 1-(4'-Amino-3'-chloro-5'-cyano-phenyl)-2-(hydroxy-tert.butylamino)-ethanol hydrochloride, m.p. 228°–230° C. (decomp.).

(r) 1-(4'-Amino-3'-chloro-5'-cyano-phenyl)-2-tert.pentylamino-ethanol hydrochloride, m.p. 218°–220° C. (decomp.).

(s) 1-(4'-Amino-3'-chloro-5'-cyano-phenyl)-2-cyclopentylamino-ethanol hydrochloride, m.p. 138°–144° C.

(t) 1-(4'-Amino-3'-chloro-5'-cyano-phenyl)-2-[1''-3,4-methylenedioxy-phenyl)-2''-propylamino]-ethanol hydrochloride, m.p. 189°–192° C.

(u) 1-(4'-Amino-3'-bromo-5'-cyano-phenyl)-2-isopropylamino-ethanol hydrochloride, m.p. 186°–189° C.

(v) 1-(4'-Amino-3'-bromo-5'-cyano-phenyl)-2-tert.butylamino-ethanol hydrochloride, m.p. 213°–215° C.

(w) 1-(4'-Amino-3'-bromo-5'-cyano-phenyl)-2-cyclobutylamino-ethanol hydrochloride, m.p. 215°–216° C. (decomp.).

(x) 1-(4'-Amino-3',5'-dicyano-phenyl)-2-cyclopropylamino-ethanol hydrochloride, m.p. 222°–223° C. (decomp.).

(y) 1-(4'-Amino-3'-trifluoromethyl-phenyl)-2-tert.butylamino-ethanol hydrochloride, m.p. 172°–174° C. (decomp.).

(z) 1-(4'-Amino-3'-trifluoromethyl-phenyl)-2-tert.pentylamino-ethanol hydrobromide, m.p. 174°–175° C. (decomp.).

(aa) 1-(4'-Amino-3'-chloro-5'-trifluoromethyl-phenyl)-2-isopropylamino-ethanol hydrochloride, m.p. 185°–187° C.

(bb) 1-(4'-Amino-3'-chloro-5'-trifluoromethyl-phenyl)-2-cyclobutylamino-ethanol hydrochloride, m.p. 177°–178° C.

(cc) 1-(4'-Amino-3'-chloro-5'-trifluoromethyl-phenyl)-2-tert.pentylamino-ethanol hydrochloride, m.p. 176°–178° C. (decomp.).

(dd) 1-(4'-Amino-3'-bromo-5'-trifluoromethyl-phenyl)-2-isopropylamino-ethanol hydrochloride, m.p. 177°–179° C. (decomp.).

(ee) 1-(4'-Amino-3'-chloro-5'-nitro-phenyl)-2-tert.butylamino-ethanol, m.p. 148°–149° C.

(ff) 1-(4'-Amino-3'-bromo-5'-nitro-phenyl)-2-tert.butylamino-ethanol, m.p. 151°–152° C.

EXAMPLE 107

1-(4'-Amino-3'-bromo-5'-fluoro-phenyl)-2-tert.butylamino-ethanol and its hydrochloride 1.5 gm of 2-tert.butylamino-1-(3'-bromo-5'-fluoro-4'-nitro-phenyl)-ethanol hydrochloride were dissolved in 40 ml of methanol. After addition of 0.6 gm of platinum dioxide, the mixture was hydrogenated, while shaking, at room temperature and normal pressure until the theoretical quantity of hydrogen had been absorbed. Thereafter, the catalyst was removed, and the solution was evaporated to dryness in vacuo. The crude, solid residue of 1-(4'-amino-3'-bromo-5'-fluoro-phenyl)-2-tert.butylamino-ethanol hydrochloride was distributed between 2N sodium hydroxide solution and methylenechloride. The organic phase was separated, washed with water, dried over sodium sulfate and evaporated to dryness in vacuo. The oily residue was chromatographically purified on a chromatography column filled with 80 gm of silicagel, using a mixture of chloroform and methanol (10:1) as the eluant. The eluates containing the desired substance were combined and evaporated to dryness in vacuo. The residue was dissolved in a small quantity of isopropanol, and the solution was acidified to a pH of 5 with ethereal hydrochloric acid. After addition of a small quantity of ether the hydrochloride crystallized out. The crystals were suction-filtered off and washed with a mixture of isopropanol and ether. M.p. 207°–208° C. (decomp.).

The following compounds were also prepared in a manner analogous to Example 107:

(a) 1-(4'-Amino-3'-fluoro-phenyl)-2-tert.butylamino-ethanol hydrochloride, m.p. 196°–197° C. (decomp.).

(b) 1-(4'-Amino-3'-chloro-5'-fluoro-phenyl)-2-isopropylamino-ethanol hydrochloride, m.p. 152°–154° C. (decomp.).

(c) 1-(4'-Amino-3'-chloro-5'-fluoro-phenyl)-2-cyclopropylamino-ethanol hydrochloride, m.p. 175°–177° C. (decomp.).

(d) 1-(4'-Amino-3'-chloro-5'-fluoro-phenyl)-2-tert.butylamino-ethanol hydrochloride, m.p. 206°–208° C. (decomp.).

(e) 1-(4'-Amino-3'-chloro-5'-fluoro-phenyl)-2-tert.pentylamino-ethanol hydrochloride, m.p. 187°–188° C. (decomp.).

(f) 1-(4'-Amino-3'-bromo-5'-fluoro-phenyl)-2-isopropylamino-ethanol hydrochloride, m.p. 171°–173° C. (decomp.).

(g) 1-(4'-Amino-3'-bromo-5'-fluoro-phenyl)-2-cyclobutylamino-ethanol hydrochloride, m.p. 164°–166° C. (decomp.).

(h) 1-(4'-Amino-3'-fluoro-5'-iodo-phenyl)-2-cyclopropylamino-ethanol hydrochloride, m.p. 199°–201° C. (decomp.).

(i) 1-(4'-Amino-3'-cyano-5'-fluoro-phenyl)-2-isopropylamino-ethanol hydrochloride, m.p. 182°–184° C. (decomp.).

(j) 1-(4'-Amino-3'-cyano-5'-fluoro-phenyl)-2-tert.butylamino-ethanol hydrochloride, m.p. 242°–243° C. (decomp.).

(k) 1-(4'-Amino-3'-cyano-phenyl)-2-cyclobutylamino-ethanol hydrobromide, m.p. > 193° C. (decomp.).

(l) 1-(4'-Amino-3'-cyano-phenyl)-2-tert.pentylamino-ethanol, m.p. 143° C.

(m) 1-(4'-Amino-3'-chloro-5'-cyano-phenyl)-2-propylamino-ethanol hydrochloride, m.p. 187°–189° C.

(n) 1-(4'-Amino-3'-chloro-5'-cyano-phenyl)-2-sec.-butylamino-ethanol dihydrochloride, m.p. 190°–191° C.

(o) 1-(4'-Amino-3'-chloro-5'-cyano-phenyl)-2-tert.butylamino-ethanol, m.p. 125°–133° C.

(p) 1-(4'-Amino-3'-chloro-5'-cyano-phenyl)-2-hydroxytert.butylamino)-ethanol hydrochloride, m.p. 228°–230° C. (decomp.).

(q) 1-(4'-Amino-3'-chloro-5'-cyano-phenyl)-2-tert.pentylamino-ethanol hydrochloride, m.p. 218°–220° C. (decomp.).

(r) 1-(4'-Amino-3'-chloro-5'-cyano-phenyl)-2-cyclopentylamino-ethanol hydrochloride, m.p. 138°–144° C.

(s) 1-(4'-Amino-3'-chloro-5'-cyano-phenyl)-2-[1''-(3,4-methylenedioxy-phenyl)-2''-propylamino]-ethanol hydrochloride, m.p. 189°–192° C.

(t) 1-(4'-Amino-3'-bromo-5'-cyano-phenyl)-2-isopropylamino-ethanol hydrochloride, m.p. 186°–189° C.

(u) 1-(4'-Amino-3'-bromo-5'-cyano-phenyl)-2-tert.butylamino-ethanol hydrochloride, m.p. 213°–215° C.

(v) 1-(4'-Amino-3'-bromo-5'-cyano-phenyl)-2-cyclobutylamino-ethanol hydrochloride, m.p. 215°–216° C. (decomp.).

(w) 1-(4'-Amino-3',5'-dicyano-phenyl)-2-tert.butylamino-ethanol hydrochloride, m.p. 251°–253° C. (decomp.).

(x) 1-(4'-Amino-3'-trifluoromethyl-phenyl)-2-tert.butylamino-ethanol hydrochloride, m.p. 172°–174° C. (decomp.).

(y) 1-(4'-Amino-3'-trifluoromethyl-phenyl)-2-tert.pentylamino-ethanol hydrobromide, m.p. 174°–175° C. (decomp.).

(z) 1-(4'-Amino-3'-chloro-5'-trifluoromethyl-phenyl)-2-isopropylamino-ethanol, m.p. 104°-106° C.

(aa) 1-(4'-Amino-3'-chloro-5'-trifluoromethyl-phenyl)-2-tert.butylamino-ethanol hydrochloride, m.p. 205°-207° C. (decomp.).

(bb) 1-(4'-Amino-3'-chloro-5'-trifluoromethyl-phenyl)-2-cyclobutylamino-ethanol hydrochloride, m.p. 177°-178° C.

(cc) 1-(4'-Amino-3'-chloro-5'-trifluoromethyl-phenyl)-2-tert.pentylamino-ethanol hydrochloride, m.p. 176°-178° C. (decomp.).

(dd) 1-(4'-Amino-3'-bromo-5'-trifluoromethyl-phenyl)-2-isopropylamino-ethanol hydrochloride, m.p. 177°-179° C. (decomp.).

EXAMPLE 108

Using a procedure analogous to that described in Example 1, 1-(4'-amino-3'-chloro-5'-trifluoromethyl-phenyl)-2-[1'''-(p-hydroxy-phenyl)-2''-propyl-amino]-ethanol, an amorphous substance having a melting point of 60°-70° C., of the formula

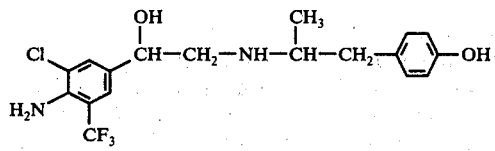

was prepared from 4'-amino-3'-chloro-2-[1''-(p-hydroxy-phenyl)-2''-propyl-amino]-5'-trifluoromethyl-acetophenone hydrochloride and sodium borohydride.

The compounds of the present invention, that is, racemic mixtures of those embraced by formula I, optically active antipode components thereof and non-toxic, pharmacologically acceptable acid addition salts of these racemic or optically active compounds, have useful pharmacodynamic properties. More particularly, they exhibit analgesic, bronchospasmolytic and utero-spasmolytic activities, and have an antispastic action on the skeletal muscles; in addition, they produce a mimetic action on the $\beta_2$-receptors and/or a blocking action on the $\beta_1$-receptors in warm-blooded animals, where, depending upon the substitution, the one or the other activity predominates. The d(+)-compounds exhibit a selective action on the $\beta_1$-receptors and the l(−)-compounds exhibit a preferred action on the $\beta_2$-receptors.

The compounds of this invention were tested for toxicity and with regard to their action on the β-receptors in warm-blooded animals, such as cats and guinea pigs, by the methods described below, and the following test results were obtained for representative species of the genus, where A = 1-(4'-Amino-3'-bromo-5'-fluoro-phenyl)-2-tert.butylamino-ethanol hydrochloride, B = 5-(4'-Amino-3'-bromo-5'-fluoro-phenyl)-3-tert.butyloxazolidine dihydrochloride, C = 1-(4'-Amino-3'-chloro-5'-fluoro-phenyl)-2-cyclopropylamino-ethanol hydrochloride, D = 1-(4'-Amino-3'-chloro-5'-fluoro-phenyl)-2-tert.butylamino-ethanol hydrochloride, E = 1-(4'-Amino-3'-fluoro-phenyl)-2-tert.butylamino-ethanol hydrochloride, F = 1-(4'-Amino-3'-trifluoromethyl-phenyl)-2-tert.pentylamino-ethanol hydrobromide, G = 1-(4'-Amino-3'-chloro-5'-trifluoromethyl-phenyl)-2-tert.butylamino-ethanol hydrochloride, H = 1-(4'-Amino-3'-chloro-5'-trifluoromethyl-phenyl)-2-cyclobutylamino-ethanol hydrochloride, I = 1-(4'-Amino-3'-chloro-5'-cyano-phenyl)-2-tert.butylamino-ethanol, J = 1-(4'-Amino-3'-bromo-5'-cyano-phenyl)-2-tert.butylamino-ethanol hydrochloride, K = 1-(4'-Amino-3'-bromo-5'-fluoro-phenyl)-2-cyclobutylamino-ethanol hydrochloride, L = 1-(4'-Amino-3'-fluoro-5'-iodo-phenyl)-2-cyclopropylamino-ethanol hydrochloride, M = 1-(4'-Amino-3'-fluoro-5'-cyano-phenyl)-2-isopropylamino-ethanol hydrochloride, N = 1-(4'-Amino-3'-fluoro-5'-cyano-phenyl)-2-tert.butylamino-ethanol hydrochloride, O = 1-(4'-Amino-3'-cyano-phenyl)-2-cyclobutylamino-ethanol hydrobromide, P = 1-(4'-Amino-3'-cyano-phenyl)-2-tert.pentylamino-ethanol, Q = 1-(4'-Amino-3'-chloro-5'-cyano-phenyl)-2-propylamino-ethanol hydrochloride, R = 1-(4'-Amino-3'-chloro-5'-cyano-phenyl)-2-sec.-butylamino-ethanol hydrochloride, S = 1-(4'-Amino-3'-chloro-5'-cyano-phenyl)-2-(hydroxy-tert.butylamino)-ethanol hydrochloride, T = 1-(4'-Amino-3'-chloro-5'-cyano-phenyl)-2-tert.pentylamino-ethanol hydrochloride, U = 1-(4'-Amino-3'-chloro-5'-cyano-phenyl)-2-cyclopentylamino-ethanol hydrochloride, V = 1-(4'-Amino-3'-chloro-5'-cyano-phenyl)-2-[1''-(3,4-methylenedioxy-phenyl)-2''-propylamino]-ethanol hydrochloride, W = 1-(4'-Amino-3'-bromo-5'-cyano-phenyl)-2-cyclobutylamino-ethanol hydrochloride, X = 1-(4'-Amino-3',5'-dicyano-phenyl)-2-tert.butylamino-ethanol hydrochloride, Y = 1-(4'-Amino-3'-bromo-5'-nitro-phenyl)-2-tert.butylamino-ethanol and Z = 1-(4'-Amino-3'-chloro-5'-nitro-phenyl)-2-tert.butylamino-ethanol.

The $\beta_1$-blocking activity was tested on anesthetized cats as antagonism to tachycardia provoked by a standard dose of 1.0 γ/kg i.v. of N-isopropyl-noradrenalin sulfate. From the average percentage reduction in heart rate acceleration caused by N-isopropyl-noradrenalin sulfate, obtained by various doses of the test compound in question, a median effective dose (ED$_{50}$) was determined by graphic extrapolation (see Tables II and III).

The $\beta_2$-mimetic activity was tested on anesthetized guinea pigs as antagonism to bronchospasm provoked by intravenous administration of 20 γ of acetylcholine per kg body weight (according to the method of Konzett-Rössler) by intravenous administration of the test compound. From the average percentage decrease of the bronchospasm produced by various doses of the test compound, a median effective dose (ED$_{50}$) was determined by graphic extrapolation (see Table I).

The $\beta_2$-blocking activity was tested on anesthetized guinea pigs as antagonism to the broncholytic activity which is observed upon administration of 5 γ/kg body weight i.v. of N-isopropyl-noradrenalin sulfate in the test arrangement according to Konzett-Rössler, following the inducement of a bronchospasm caused by a standard dose of 20 γ/kg body weight i.v. of acetylcholine (see Table III).

The acute toxicity of the compounds was determined on groups of 10 mice. The LD$_{50}$, i.e. the dose administered intravenously after which 50% of the animals died within a period of 14 days, was calculated according to the method of Litchfield and Wilcoxon (see Tables II and III).

TABLE I

| Compound | $\beta_2$-mimetic activity | | | Duration of activity |
|---|---|---|---|---|
| | $n_1$ | $n_2$ | $ED_{50}\gamma$/kg i.v. | minutes |
| A | 9 | 5 | 8.3 | >150 |
| B | 5 | 4 | 6.7 | >110 |
| C | 5 | 4 | 24.0 | >50 |
| D | 5 | 4 | 19.0 | >120 |
| E | 6 | 3 | 18.0 | >80 |
| G | 10 | 5 | 19.5 | >130 |
| H | 5 | 5 | 6.8 | >125 |
| I | 11 | 4 | 0.20 | >95 |
| J | 5 | 4 | 4.8 | >40 |
| K | 6 | 3 | 58.0 | >50 |
| M | 6 | 4 | 0.08 | >40 |
| N | 5 | 3 | 0.32 | >40 |
| O | 5 | 3 | 6.9 | 40 |
| P | 5 | 4 | 3.6 | 65 |
| Q | 5 | 3 | 27.0 | 50 |
| R | 5 | 3 | 5.7 | >80 |
| S | 5 | 3 | 10.0 | >65 |
| T | 5 | 3 | 1.9 | >40 |
| U | 4 | 4 | 9.8 | >50 |
| V | 6 | 4 | 2.7 | >65 |
| W | 5 | 3 | 20.5 | >50 |
| X | 6 | 3 | 11.3 | >65 |
| Z | 5 | 3 | 31.5 | >80 |

$n_1$ = number of animals/dose;
$n_2$ = number of doses taken into consideration for the calculation of the $ED_{50}$

TABLE II

| Compound | Blocking action on the $\beta_1$-receptors | | | $LD_{50}$ mgm/kg |
|---|---|---|---|---|
| | $n_1$ | $n_2$ | $ED_{50}$ $\gamma$/kg i.v. | i.v. |
| A | 3 | 5 | 18.5 | 34.5 |
| B | — | — | — | 27.2 |
| C | 4 | 5 | 14.0 | 57.0 |
| D | 4 | 5 | 8.0 | 35.1 |
| E | 4 | 5 | 13.5 | 69.2 |
| F | 3 | 5 | 35.0 | — |
| G | 5 | 5 | 11.5 | 36.5 |
| H | — | — | — | 36.3 |
| I | 5 | 5 | 0.74 | 60.0 |
| J | — | — | — | 67.0 |
| K | 4 | 4 | 1.5 | 26.4 |
| L | 6 | 5 | 1.3 | 45.2 |
| M | 5 | 3 | 0.27 | 66.4 |
| N | 6 | 4 | 0.022 | 58.4 |
| O | 5 | 5 | 0.070 | 61.8 |
| P | 5 | 5 | 0.086 | 62.0 |
| Q | 6 | 5 | 0.76 | 53.4 |
| R | 6 | 6 | 0.32 | 40.4 |
| S | 5 | 4 | 0.76 | 81.8 |
| T | 5 | 4 | 0.45 | 33.7 |
| U | 6 | 4 | 0.70 | 39.1 |
| V | 6 | 4 | 1.4 | 13.5 |
| W | 6 | 5 | 0.078 | 38.5 |
| X | 6 | 4 | 0.92 | 166.0 |
| Y | 5 | 4 | 2.8 | 35.8 |
| Z | 6 | 4 | 4.5 | 42.4 |

$n_1$ = number of animals/dose
$n_2$ = number of doses used in calculation of $ED_{50}$

TABLE III

| Compound | Blocking Action on $\beta_1$-receptors | | | Blocking Action on $\beta_2$-receptors | | | mgm/kg i.v. |
|---|---|---|---|---|---|---|---|
| | $n_1$ | $n_2$ | $ED_{50}$ $\gamma$/kg i.v. | $n_1$ | n | $ED_{50}$ $\gamma$/kg i.v. | |
| A-d(+) | 7 | 4 | 8.4 | 5 | 1 | >2000 | 37.2 |
| D-d(+) | 6 | 4 | 6.2 | 5 | 1 | >2000 | 34.2 |
| E-d(+) | 8 | 3 | 1.5 | 4 | 1 | >2000 | — |
| G-d(+) | 8 | 4 | 12.5 | 4 | 1 | >2000 | 33.2 |

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.016 to 1.67 $\gamma$/kg body weight, preferably 0.08 to 0.83 $\gamma$/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 109

Tablets

The tablet composition is compounded from the following ingredients:

| | | |
|---|---|---|
| 1-(4'-Amino-3'-chloro-5'-cyano-phenyl)-2-tert.butylamino-ethanol hydrochloride | 0.01 | parts |
| Lactose | 82.49 | " |
| Potato starch | 33.00 | " |
| Polyvinylpyrrolidone | 4.00 | " |
| Magnesium stearate | 0.50 | " |
| Total | 120.00 | parts |

Preparation:

The active ingredient and the polyvinylpyrrolidone are dissolved in ethanol, and the resulting solution is used to uniformly moisten a homogeneous mixture of the lactose and the potato starch. The moist mass is granulated through a 1.5 mm-mesh screen, the granulate is dried at 50° C. and again passed through a 1.0 mm-mesh screen, the resulting dry granulate is admixed with the magnesium stearate, and the composition is compressed into 120 mgm-tablets in a conventional tablet making machine. Each tablet contains 10 $\gamma$ of the active ingredient and is an oral dosage unit composition with effective bronchospasmolytic action.

EXAMPLE 110

Coated pills

The pill core composition is compounded from the following ingredients:

| | | |
|---|---|---|
| d-(+)-1-(4'-Amino-3'-fluoro-phenyl)-2-tert.butylamino-ethanol hydrochloride | 0.025 | parts |
| Lactose | 82.475 | " |
| Potato starch | 33.000 | " |
| Polyvinylpyrrolidone | 4.000 | " |
| Magnesium stearate | 0.500 | " |
| Total | 120.000 | parts |

Preparation:

The pill core composition is compounded in the same manner as the tablet composition in Example 109, and the composition is compressed into 120 mgm-pill cores which are subsequently coated with a thin shell consisting essentially of sugar and talcum and finally polished with beeswax. Each coated pill contains 25 $\gamma$ of the active ingredient and is an oral dosage unit composition with effective bronchospasmolytic action.

| | | |
|---|---|---|
| 1-(4'-Amino-3'-chloro-5'-trifluoro-methyl-phenyl)-2-tert.butylamino-ethanol hydrochloride | 0.010 | parts |
| Lactose | 59.990 | " |
| Corn starch | 60.000 | " |
| Total | 120.000 | parts |

Preparation:

The active ingredient, the lactose and the corn starch are intimately admixed with each other, and 120 mgm-portions of the mixture are filled into gelatin capsules of suitable size. Each capsule contains 10 γ of the active ingredient and is an oral dosage unit composition with effective bronchospasmolytic action.

EXAMPLE 112

Hypodermic solution

The solution if compounded from the following ingredients:

| | | |
|---|---|---|
| 1-(4'-Amino-3'-bromo-5'-fluoro-phenyl)-2-tert.butylamino-ethanol hydrochloride | 0.01 | parts |
| Citric acid | 2.5 | " |
| Sodium acid phosphate | 7.5 | " |
| Sodium chloride | 4.6 | " |
| Double-distilled water    q.s.ad | 2000 | " by vol. |

Preparation:

The active ingredient, the buffers and the sodium chloride are dissolved in the distilled water, the solution is filtered until free from suspended matter, and the filtrate is filled, in an inert atmosphere of nitrogen, into 2 cc-brown ampules which are then sealed and sterilized for 20 minutes at 120° C. Each ampule contains 10 γ of the active ingredient, and the contents thereof are an injectable dosage unit composition with effective bronchospasmolytic action.

EXAMPLE 113

Rectal Suppositories

The suppository composition is compounded from the following ingredients:

| | | |
|---|---|---|
| 1-(4'-Amino-3'-chloro-5'-cyano-phenyl)-2-tert.butylamino-ethanol | 0.01 | parts |
| Suppository base (e.g. cocoa butter) | 1699.99 | " |
| Total | 1700.00 | parts |

Preparation:

The finely pulverized active ingredient is stirred, with the aid of an immersion homogenizer, into the suppository base which had previously been melted and cooled to 40° C. 1.7 gm-portions of the mixture are poured at 37° C. into cooled suppository molds and allowed to harden therein. Each suppository contains 10 γ of the active ingredient and is a rectal dosage unit composition with effective bronchospasmolytic action.

EXAMPLE 114

Syrup

The syrup is compounded from the following ingredients:

| | | |
|---|---|---|
| d-(+)-1-(4'-Amino-3'-fluoro-phenyl)-2-tert.butylamino-ethanol hydrochloride | 0.0001 | parts |
| Benzoic acid | 0.1 | " |
| Tartaric acid | 1.0 | parts |
| Sugar | 50.0 | " |
| Flavoring | 1.0 | " |
| Food color | 0.05 | " |
| Distilled water | 100.0 | " |

Preparation:

About 60 parts of distilled water are heated to 80° C., the benzoic acid, the tartaric acid, the active ingredient, the food color and the sugar are successively dissolved therein, the solution is allowed to cool to room temperature, the flavoring is added, the remaining amount of distilled water added, and the resulting syrup is filtered. Each 10 ml of the syrups contain 10 γ of the active ingredient and are an oral dosage unit composition with effective bronchospasmolytic action.

Analogous results are obtained when any one of the other racemic or optically active compounds embraced by formula I or a non-toxic acid addition salt thereof is substituted for the particular active ingredient in Examples 109 through 114. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A racemic mixture or optically active antipode of a compound of the formula

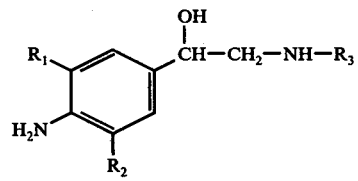

wherein $R_1$ is fluorine, chlorine, bromine, iodine or cyano, $R_2$ is trifluoromethyl, nitro or cyano, and $R_3$ is alkyl of 3 to 5 carbon atoms, hydroxy(alkyl of 3 to 5 carbon atoms), cycloalkyl of 3 to 5 carbon atoms, 1-(3,4-methylenedioxy-phenyl)-2-propyl or 1-(p-hydroxy-phenyl)-2-propyl, or a non-toxic, pharmacologically acceptable acid addition salt thereof.

2. A compound of claim 1, which is 1-(4'-amino-3'-chloro-5'-trifluoromethyl-phenyl)-2-tert.butylamino-ethanol or a non-toxic, pharmacologically acceptable acid addition salt thereof.

3. A compound of claim 1, which is 1-(4'-amino-3'-chloro-5'-trifluoromethyl-phenyl)-2-cyclobutylamino-ethanol or a non-toxic, pharmacologically acceptable acid addition salt thereof.

4. A compound of claim 1, which is 1-(4'-amino-3'-chloro-5'-cyano-phenyl)-2-tert.butylamino-ethanol or a nontoxic, pharmacologically acceptable acid addition salt thereof.

5. A compound of claim 1, which is 1-(4'-amino-3'-bromo-5'-cyano-phenyl)-2-tert.butylamino-ethanol or a nontoxic, pharmacologically acceptable acid addition salt thereof.

6. A pharmaceutical dosage unit composition consisting essentially of an inert pharmaceutical carrier and an effective bronchospasmolytic amount of a compound of claim 1.

7. The method of antagonizing bronchospasms in a warm-blooded animal in need of such treatment, which comprises perorally, parenterally or rectally administering to said animal a compound of claim 1.

* * * * *

UNITED STATES PATENT OFFICE
CERTIFICATE OF CORRECTION

Patent No. 4,119,710          Dated October 10, 1978

Inventor(s) GUNTHER ENGELHARDT, JOHANNES KECK, GERD KRÜGER KLAUS-REINHOLD NOLL, and HELMUT PIEPER It is certified that error appears in the above-identified patent and that said Letters Patent are hereby corrected as shown below:

Col. 13, line 7, "was" should read --were--.

Col. 20, line 13, "menthoxy-cabonyl]" should read

--menthoxy-carbonyl]--.

Col. 23, line 68, "228°-230° L C." should read --228°-230°C.--

Col. 31, line 53, "n" should read --$n_2$--.

Col. 32, between lines 60 and 61, insert the following:

--EXAMPLE 111

Gelatin capsules

The capsule filler composition is compounded from the following ingredients:--

Signed and Sealed this

Thirteenth Day of March 1979

[SEAL]

Attest:

RUTH C. MASON
Attesting Officer

DONALD W. BANNER
Commissioner of Patents and Trademarks